US008916162B2

(12) United States Patent
Zdanovsky

(10) Patent No.: US 8,916,162 B2
(45) Date of Patent: Dec. 23, 2014

(54) BOTULINUM NEUROTOXIN ANTIGENIC COMPOSITIONS AND METHODS

(76) Inventor: Alexey Gennadievich Zdanovsky, Madison, WI (US)

( * ) Notice: Subject to any disclaimer, the term of this patent is extended or adjusted under 35 U.S.C. 154(b) by 0 days.

(21) Appl. No.: 13/579,853

(22) PCT Filed: Feb. 18, 2011

(86) PCT No.: PCT/US2011/025482

§ 371 (c)(1),
(2), (4) Date: Aug. 17, 2012

(87) PCT Pub. No.: WO2011/103465

PCT Pub. Date: Aug. 25, 2011

(65) Prior Publication Data

US 2012/0328642 A1    Dec. 27, 2012

Related U.S. Application Data

(60) Provisional application No. 61/338,477, filed on Feb. 20, 2010.

(51) Int. Cl.
*A61K 39/38* (2006.01)
*A61K 39/40* (2006.01)
*A61K 39/385* (2006.01)
*A61K 39/116* (2006.01)
*A61K 39/08* (2006.01)
*A61K 39/00* (2006.01)

(52) U.S. Cl.
CPC ........... *A61K 39/08* (2013.01); *A61K 2039/605* (2013.01)
USPC .................... 424/183.1; 424/1.69; 424/143.1; 424/150.1; 424/156.1; 424/163.1; 424/164.1; 424/167.1; 424/178.1; 424/184.1; 424/192.1; 424/193.1; 424/197.11; 424/203.1; 424/234.1; 424/236.1; 424/239.1; 424/418

(58) Field of Classification Search
CPC . A61K 38/16; A61K 38/164; A61K 38/4893; A61K 39/00; A61K 47/48261; A61K 2039/00; A61K 2039/02; A61K 2039/58; A61K 2039/60; A61K 2039/64; A61K 2039/62; A61K 2039/70; A61K 2039/6031; A61K 2039/6037; A61K 2039/6068; A61K 2039/55516; A61K 2039/55544; C12N 9/52; C12N 15/03; C07K 141/33; C07K 14/24; C07K 14/195; C07K 2319/00; C07K 2319/20; C07K 2319/21; C07K 2319/40; C07K 2139/55; C07K 2319/70; C07K 2319/80; C07K 2319/85
See application file for complete search history.

(56) References Cited

U.S. PATENT DOCUMENTS 5,851,827 A * 12/1998 Titball et al. ................... 435/325
(Continued)

FOREIGN PATENT DOCUMENTS

WO    WO-2008/036682       3/2008
WO    WO 2008-036682    *  3/2008 ............. A61K 38/17

OTHER PUBLICATIONS

Battey, F.D., et al., "The 39-kDa receptor-associated protein regulates ligand binding by the very low density lipoprotein receptor," J. Biol. Chem., vol. 269, Issue 37, (Sep. 1994), pp. 23268-2327.
(Continued)

*Primary Examiner* — Ja'Na Hines
(74) *Attorney, Agent, or Firm* — Foley & Lardner, LLP

(57) ABSTRACT

Methods and compositions pertaining to botulinum neurotoxin (BoNT) light chain epitopes are provided. In particular, the methods and compositions relate to the use of real and mimetic BoNT light chain epitopes for generating an immune response in a subject, and for immunization against BoNT toxicity. Methods and compositions for detecting, isolating, and purifying BoNT epitopes and anti-BoNT antibodies are also provided.

11 Claims, 7 Drawing Sheets

```
  1   MQFVNKQFNY KDPVNGVDIA YIKIPNVGQM QPVKAFKIHN KIWVIPERDT
 51   FTNPEEGDLN PPPEAKQVPV SYYDSTYLST DNEKDNYLKG VTKLFERIYS
101   TDLGRMLLTS IVRGIPFWGG STIDTELKVI DTNCINVIQP DGSYRSEELN
151   LVIIGPSADI IQFECKSFGH EVLNLTRNGY GSTQYIRFSP DFTFGFEESL
201   EVDTNPLLGA GKFATDPAVT LAHELIHAGH RLYGIAINPN RVFKVNTNAY
251   YEMSGLEVSF EELRTFGGHD AKFIDSLQEN EFRLYYYNKF KDIASTLNKA
301   KSIVGTTASL QYMKNVFKEK YLLSEDTSGK FSVDKLKFDK LYKMLTEIYT
351   EDNFVKFFKV LNRKTYLNFD KAVFKINIVP KVNYTIYDGF NLRNTNLAAN
401   FNGQNTEINN MNFTKLKNFT GLFEFYKLLC VRGIITSKTK SLDKGYNK
```

```
Adel1                    VPVSYYDSTYLST
Adel1-1  FTNPEEGDLNPPPEAKQVPVSYYDSTYLST
Adel1-2                   VPVSYYDSTYLSTDNEKDNYLKG Adel2    DFTFGFEESLEVDTNPLLG
Adel2-1  SPDFTFGFEESLEVDTNPLLGAGKFATDP Adel3    KMLTEIYTEDNFVKFFKVLNRKTYLNFDKAVFKINIVPKVNYTIYDGFNLRNTNLAAN Adel4    FNGQNTEINNMNFTKLKNFTGLF
Adel4-1  FNGQNTEINNMNFTK
Adel4-2  FNGQNTEINNMNFTKLKNFTGLFEFYK
```

(56) References Cited

U.S. PATENT DOCUMENTS

| | | |
|---|---|---|
| 7,462,699 B2 | 12/2008 | Atassi |
| 7,829,537 B2 | 11/2010 | Zankel et al. |
| 2003/0185850 A1 | 10/2003 | Dertzbaugh |
| 2003/0215468 A1* | 11/2003 | Williams et al. ............ 424/239.1 |
| 2005/0042227 A1* | 2/2005 | Zankel et al. ............... 424/178.1 |
| 2005/0260230 A1* | 11/2005 | Steward et al. ............. 424/239.1 |
| 2006/0233825 A1 | 10/2006 | Jayappa et al. |

OTHER PUBLICATIONS

Dertzbaugh M.T., et al., "Mapping of protective and cross-reactive domains of the type A neurotoxin of *Clostridium botulinum*," Vaccine, vol. 14, (1996), pp. 1538-1544.

International Preliminary Report on Patentability received for PCT/US2011/025482 mailed Aug. 30, 2012 (8 pages).

International Search Report and Written Opinion of the International Searching Authority in PCT Application No. PCT/US2011/025482 mailed Dec. 22, 2011 (14 pages).

* cited by examiner

FIGURE 1

```
  1    MQFVNKQFNY  KDPVNGVDIA  YIKIPNVGQM  QPVKAFKIHN  KIWVIPERDT
 51    FTNPEEGDLN  PPPEAKQVPV  SYYDSTYLST  DNEKDNYLKG  VTKLFERIYS
101    TDLGRMLLTS  IVRGIPFWGG  STIDTELKVI  DTNCINVIQP  DGSYRSEELN
151    LVIIGPSADI  IQFECKSFGH  EVLNLTRNGY  GSTQYIRFSP  DFTFGFEESL
201    EVDTNPLLGA  GKFATDPAVT  LAHELIHAGH  RLYGIAINPN  RVFKVNTNAY
251    YEMSGLEVSF  EELRTFGGHD  AKFIDSLQEN  EFRLYYYNKF  KDIASTLNKA
301    KSIVGTTASL  QYMKNVFKEK  YLLSEDTSGK  FSVDKLKFDK  LYKMLTEIYT
351    EDNFVKFFKV  LNRKTYLNFD  KAVFKINIVP  KVNYTIYDGF  NLRNTNLAAN
401    FNGQNTEINN  MNFTKLKNFT  GLFEFYKLLC  VRGIITSKTK  SLDKGYNK
```

Adel1            VPVSYYDSTYLST
Adel1-1    FTNPEEGDLNPPPEAKQVPVSYYDSTYLST
Adel1-2              VPVSYYDSTYLSTDNEKDNYLKG Adel2      DFTFGFEESLEVDTNPLLG
Adel2-1    SPDFTFGFEESLEVDTNPLLGAGKFATDP Adel3      KMLTEIYTEDNFVKFFKVLNRKTYLNFDKAVFKINIVPKVNYTIYDGFNLRNTNLAAN

Adel4      FNGQNTEINNMNFTKLKNFTGLF
Adel4-1    FNGQNTEINNMNFTK
Adel4-2    FNGQNTEINNMNFTKLKNFTGLFEFYK

```
BoNT/A-L  (65)   AKQ VPVSYYDSTYLST DNE--
BoNT/C-L  (64)   VTS PKSGYYDPNYLST DSN--
BoNT/D-L  (64)   PTS KYQSYYDPSYLST DEQ--
BoNT/B-L  (66)   FNR DVCEYYDPDYLNT NDK--
BoNT/G-L  (66)   FSK DVYEYYDPTYLKT DAE--
TeNT-L    (65)   LIE GASEYYDPNYLRT DSD--
BoNT/E-L  (64)   LKN GDSEYYDPNYLQS DHE--
BoNT/F-L  (65)   LEN GSSAYYDPNYLST DAE--
                     del1

BoNT/A-L  (186)  IRFSP NKTFGFEESLEVDTNPLLG AG----HELIHAGHRLYGI--
BoNT/C-L  (192)  ISISP RPMLTYSNATNDVGEGRFS KS----HELNHAMHNLYGI--
BoNT/D-L  (192)  LKVAP EFLLYFSDVTSHQSSAVLG KS----HELTHSLHQLYGI--
BoNT/B-L  (193)  NKFCP EYVSVFNNVQENKGASIFN RR----HELIHVLHGLYGI--
BoNT/G-L  (193)  IRFCP SCLNVFNNVQENKDTSIFS RR----HELIHVLHGLYGI--
TeNT-L    (196)  NAFCP EYVPTFDNVIENITSLTIG KS----HELIHVLHGLYGM--
BoNT/E-L  (187)  NTFSP EYSFRFNDHS---------- MN----HELIHSLHGLYGA--
BoNT/F-L  (193)  NTFSP EYEYIFNDISGGY----NSS TE----HELIHALHGLYGA--
                       del2                      Zn BoNT/A-L  (333)  VDKLKFDKLY NNLTEIYTEDHFVKFKVLNRKTYLNFDK-AVFKINIVPK
BoNT/C-L  (342)  VSRNKFVELY HELTQIFTEFNYAKIYNVQNRKIYLSNVY-TPVTANILDD
BoNT/D-L  (342)  VSIDKFNSLY SDLTHVMSEVVYSSQINVKNRTHYFSRHY-LPVFANILDD
BoNT/B-L  (340)  IDVSFDKLY  KSLMFGFTETNIAENYKIKTRASYFSDSLPPVKIKNLLDN
BoNT/G-L  (339)  VDKNKFDKLY KALMFGFTETNIAGEYGIKTRYSYFSEYLPPIKTEKLLDN
TeNT-L    (342)  VNEDKFQILY NSIMYGFTEIELGKKFNIKTRLSYFSMNHDPVKIPNLLDD
BoNT/E-L  (322)  YRINKFND IY KKLYS-FTEFDLATKFQVRCRQTYIGQYK-YFKLSNLLND
BoNT/F-L  (336)  VNENKFNE IY KKLYS-FTEIDLANKFKVRCRNTYFIKYG-FLKVPNLLDD
                                                              del3

BoNT/A-L  (382)  VNYTIYDGFNLRNTNLAAN FNGQNTEINNMNFTK NKNFTGLFEFYKLLCV
BoNT/C-L  (391)  NVYDIQNGFNIPKSNLNVL FMGQNLSRNP-NLRK VNPEN-NLYLFTKFCH
BoNT/D-L  (391)  NIYTIRDGFNLTHKGFNIE NSGQNIERNP-NLQK LSES-VVDLFTKYCL
BoNT/B-L  (390)  EIYTIEEGFNISDKDNEKE YRGQNKAINKQAYEE ISKEH-LAVYKTCNCK
BoNT/G-L  (389)  TIYTQNEGFNIASKNLKT  FNGQNKAVNKEAYEE ISLEH-LVIYRIANCK
TeNT-L    (392)  TIYNDTEGFNIESKDLKSE YRGQNMRVNTHAFRN VDSSG-LVSKLIGLCK
BoNT/E-L  (370)  SIYNISEGYNIN--NLKVN FRGQNAHLNPRIITP ITGPG-LVKKINFCK
BoNT/F-L  (384)  DIYTVSEGFNIG--NLAVN NRGQNIKLNPKIIDS IPDKG-LVEKIVKFCK
                                      del4

HisbioRAP-FBAdel1s: Molecular weight: 50,341.91 Da

```
  1  MGSSHHHHHH SSGLVPRGSH MLDMASSLRQ ILDSQKMEWR SNAGGSGRDN
 51  RVISREKNQP KPSPKRESGE EFRMEKLNQL WEKAQRLHLP PVRLAELHAD
101  LKIQERDELA WKKLKLDGLD EDGEKEARLI RNLNVILAKY GLDGKKDARQ
151  VTSNSLSGTQ EDGLDDPRLE KLWHKAKTSG KFSGEELDKL WREFLHHKEK
201  VHEYNVLLET LSRTEEIHEN VISPSDLSDI KGSVLHSRHT ELKEKLRSIN
251  QGLDRLRRVS HQGYSTEAEF EEPRVIDLWD LAQSANLTDK ELEAFREELK
301  HFEAKIEKHN HYQKQLEIAH EKLRHAESVG DGERVSRSRE KHALLEGRTK
351  ELGYTVKKHL QDLSGRISRA RHNELERPVP GSGSSAYYDP NYLTTVERPV
401  PGSDVCEYYD PDYLNTVERP VPGSVPVSYY DSTYLST
```

α-Tox-FBAdel1s: Molecular weight: 52,866.72 Da

```
  1  MKRKICKALV CATLVTSLWA GVSTKVYAWD GKIDGTGTHA MIVTQGVSIL
 51  ENDMSKNEPE SVRKNLEILK DNMHELQLGS TYPDYDKNAY DLYQDHFWDP
101  DTNNNFSKDN SWYLAYSIPD TGESQIRKFS ALARYEWQRG NYKQATFYLG
151  EAMHYFGDID TPYHPANVTA VDSAGHVKFE TFAEERKEQY KINTVGCKTN
201  EDFYADILKN KDFNAWSKEY ARGFAKTGKS IYYSHASMSH SWDDWDYAAK
251  VTLANSQKGT AGYIYRFLHD VSEGNDPSVG NNVKELVAYI STSGEKDAGT
301  DDYMYFGIKT KDGKTQEWEM DNPGNDFMAG SKDTYTFKLK DENLKIDDIQ
351  NMWIRKRKYT AFPDAYKPEN IKVIANGKVV VDKDINEWIS GNSTYNIKSS
401  GDLERPVPGS GSSAYYDPNY LTTVERPVPG SDVCEYYDPD YLNTVERPVP
451  GSVPVSYYDS TYLST
```

SChoB-BoNT/Amimetic1-8: Molecular weight: 34,923.78 Da

```
  1  MNKVKCYVLF TALLSSLCAY GASSYAHGTP QNITDLCAES HNTQIYTLND
 51  KIFSYTESLA GKREMAIITF KNGAIFQVEV PSSQHIDSQK KAIERMKDTL
101  RIAYLTEAKV EKLCVWNNKT PHAIAAISMA NGGSGVPGSG GSGQAPLSLV
151  QPFRDSAAAD VPGSGGSGYS YWDSTFLDTL SAAADVPGSG GSGVGADVGT
201  LSAAFSAAAD VPGSGGSGDV GDLGRPVHFI SAAADVPGSG GSGAPTSPVT
251  HGPQLSAAAD VPGSGGSGSL TSPITPRPEY SAAADVPGSG GSGDFGDHNP
301  PEQSSSAAAD VPGSGGSGDP TRFHSRPPAI SAAADVQLQV EHHHHHH
```

HisbioRAP-BoNT/Amimetic1-8: Molecular weight: 62,879.90 Da

```
  1  MGSSHHHHHH SSGLVPRGSH MLDMASSLRQ ILDSQKMEWR SNAGGSGRDN
 51  RVISREKNQP KPSPKRESGE EFRMEKLNQL WEKAQRLHLP PVRLAELHAD
101  LKIQERDELA WKKLKLDGLD EDGEKEARLI RNLNVILAKY GLDGKKDARQ
151  VTSNSLSGTQ EDGLDDPRLE KLWHKAKTSG KFSGEELDKL WREFLHHKEK
201  VHEYNVLLET LSRTEEIHEN VISPSDLSDI KGSVLHSRHT ELKEKLRSIN
251  QGLDRLRRVS HQGYSTEAEF EEPRVIDLWD LAQSANLTDK ELEAFREELK
301  HFEAKIEKHN HYQKQLEIAH EKLRHAESVG DGERVSRSRE KHALLEGRTK
351  ELGYTVKKHL QDLSGRISRA RHNELERPVP GSGGSGQAPL SLVQPFRDSA
401  AADVPGSGGS GYSYWDSTFL DTLSAAADVP GSGGSGVGAD VGTLSAAFSA
451  AADVPGSGGS GDVGDLGRPV HFISAAADVP GSGGSGAPTS PVTHGPQLSA
501  AADVPGSGGS GSLTSPITPR PEYSAAADVP GSGGSGDFGD HNPPEQSSSA
551  AADVPGSGGS GDPTRFHSRP PAISAAADVQ LD
```

/ # BOTULINUM NEUROTOXIN ANTIGENIC COMPOSITIONS AND METHODS

CLAIM OF PRIORITY

This application is the U.S. National Stage of PCT/US2011/025482, filed Feb. 18, 2011, which claims priority to U.S. Provisional Application 61/338,477, filed Feb. 20, 2010, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Jul. 31, 2012, is named 09952301.txt and is 59,774 bytes in size.

FIELD OF INVENTION

The present technology relates to antigenic compositions of botulinum neurotoxin (BoNT), and methods for detecting, isolating, or purifying BoNT epitopes and anti-BoNT antibodies. Method of using such epitopes and antibodies are also disclosed.

BACKGROUND

The following description is provided to assist the understanding of the reader. None of the information provided or references cited is admitted to be prior art to the present disclosure.

The seven serologically distinct botulinum neurotoxins produced by *Clostridium botulinum, Clostridium argentiensis*, and *Clostridium baratti*, (BoNT/A, /B, /C, /D, /E, /F, /G) are some of the most potent toxins known to mankind. These homologous toxins specifically target neurons and act through the interruption of neurotransmission. This interruption results in muscle paralysis, which in severe cases of intoxication leads to death from asphyxiation in humans and animals. Human botulism is typically caused by serotypes A, B, E, and occasionally F. Serotypes C and D cause toxicity only in non-human animals.

A single molecule of each toxin possesses three functional domains: receptor-recognition, transport and catalytic. The catalytic domains are $Zn^{2+}$ metalloproteases that recognize and selectively cleave proteins involved in targeting of presynaptic vesicles and their fusion with the neuronal plasma membrane, in this way neurotoxins block neurotransmitter release into the synaptic cleft. Although there is a certain degree of homology between different clostridial neurotoxins, their catalytic domains recognize different substrates: BoNT/B, /D, /F and /G cleave synaptobrevin 2; BoNT/A, /C and /E cleave synaptosomal-associated protein of 25 kDa (SNAP25); BoNT/C cleaves syntaxin.

Botulinum neurotoxins are synthesized as single polypeptides approximately 1500 amino acids in length (Mr~150 kDa), and then cleaved into heavy and light chains (Mr~100 kDa, Mr~50 kDa), which are held together by a disulfide bond. The light chain corresponds to the catalytic domain while heavy chains carry the receptor-recognition and transport domains, and are responsible for transport of corresponding light chains into the cytosol of neuronal cells.

Currently, botulinum neurotoxins are viewed as potent biological warfare agents. At the same time, botulinum neurotoxins of serotypes A and B are extensively used in medicine as drugs for the treatment of strabismus, blepharospasms, migraines and many other neurological conditions. The toxins are also commonly used as cosmetic agents.

In recent years, several researchers have used a series of synthetic BoNT/A peptides to map epitopes recognized by antisera from several species, including humans, and peptide displays of BoNT/A to map epitopes recognized by monoclonal antibodies. Others have reported epitopes recognized by neutralizing anti-BoNT antibodies. Thus far, however, epitope mapping efforts have focused on the heavy chains of botulinum neurotoxins.

SUMMARY

In one embodiment, the present disclosure relates to an antigenic composition comprising: a carrier peptide and at least one epitope, wherein the carrier peptide is selected from the group consisting of Receptor Associated Protein (RAP), *Clostridium perfringens* α-toxin, and cholera toxin subunit B, and wherein the carrier peptide and the epitope comprise a fusion protein. Additionally or alternatively, in some embodiments, the epitope comprises a real or mimetic botulinum neurotoxin (BoNT) epitope. In some embodiments, the epitope is capable of eliciting an immune response in a human or animal subject. Additionally or alternatively, in some embodiments, the fusion protein specifically binds to an anti-BoNT antibody. In another embodiment, the real or mimetic epitope includes one or more of the sequences given in FIG. 3 or Tables 3-5.

In some embodiments, the fusion protein is encoded by a polynucleotide. Additionally or alternatively, in some embodiments, the polynucleotide is provided, in an expression vector. In another embodiment, the expression vector is selected from the group consisting of a plasmid DNA, a viral vector, a bacterial vector, and a mammalian vector. Typically, the vector is capable of autonomous replication in a host cell. In another embodiment, the vector is capable of integrating into the genome of the host.

In some embodiments, the present disclosure relates to an antigenic composition comprising multiple real and/or multiple mimetic BoNT epitopes. In some embodiments, at each epitope is capable of individually eliciting an immune response in a human or animal subject. Additionally or alternatively, in some embodiments, administering a therapeutically effective amount of the composition to the subject elicits multiple immune responses directed to multiple epitopes. In some embodiments, each epitope specifically binds to an anti-BoNT antibody.

In some embodiments, the present disclosure relates to a method for producing an antigenic composition comprising (a) expressing in a host cell a fusion protein comprising a carrier peptide and at least one epitope, wherein the carrier peptide is selected from the group consisting of Receptor Associated Protein (RAP), *Clostridium perfringens* α-toxin, and cholera toxin subunit B. In some embodiments, the epitope of the fusion protein is antigenic. In further embodiments, the methods include the step of isolating the fusion protein from the host. In some embodiments, the epitope comprises a real or mimetic botulinum neurotoxin (BoNT) epitope. In some embodiments, the epitope is capable of eliciting an immune response in a human or animal subject. In some embodiments, the real or mimetic epitope is selected from the epitopes shown in FIG. 3 or Tables 3-5. In another embodiment, the fusion protein is expressed in the host cell from an expression vector. In another embodiment, the expression vector is selected from the group consisting of a plasmid DNA, a viral vector, a bacterial vector, and a mammalian vector. Typically, the vector is capable of autonomous replication in a host cell. In another embodiment, the vector is capable of integrating into the genome of the host cell. In another embodiment, the fusion protein comprises a carrier peptide and multiple real and/or multiple mimetic BoNT epitopes. In some embodiments, the epitopes are capable of individually eliciting an immune response in a human or animal subject.

In one embodiment, the present disclosure relates to a method for isolating a real or mimetic BoNT epitope from a host cell comprising: expressing the epitope as a fusion protein with a Receptor Associated Protein (RAP) carrier peptide, wherein the carrier peptide enhances the solubility of said epitope. In some embodiments, the host cell is *E. coli*. In some embodiments, the fusion protein is isolated from solution.

In one embodiment, the present disclosure relates to a method for isolating a real or mimetic BoNT epitope from a host cell comprising: expressing the epitope as a fusion protein with a *Clostridium perfringens* α-toxin carrier peptide, wherein the fusion protein is secreted by the host cell into the culture medium. In some embodiments, the host cell is *E. coli*. In some embodiments, the fusion protein is isolated from the culture medium.

In one embodiment, methods are provided for isolating or purifying anti-BoNT antibodies from a sample comprising: (a) contacting the sample with a biochemically effective amount of a BoNT epitope-containing composition under conditions conducive to specific epitope-antibody binding; (b) removing non-specifically bound contaminants; (c) altering conditions to release bound antibodies; and (d) recovering the released antibodies.

In one embodiment, methods are provided for detecting the presence of anti-BoNT antibodies in a sample comprising: (a) contacting the sample with a diagnostically effective amount of a BoNT epitope-containing composition under conditions conducive to specific epitope-antibody binding, and (b) detecting the antibodies.

In one embodiment, methods are provided for diagnosing the exposure of a human or animal subject to BoNT comprising: (a) contacting a biological sample front the subject with a diagnostically effective amount of a composition comprising at least one BoNT epitope under conditions conducive to specific epitope-antibody binding. In some embodiments, the methods include the step of contacting the sample with an appropriate secondary detection reagent. In one embodiment, the sample is a cell, tissue, or bodily fluid. In some embodiments, the BoNT epitope is fused to a carrier protein.

In one embodiment, the present disclosure relates to a method of immunizing a human or animal subject against BoNT toxicity comprising: administering to the subject a therapeutically effective amount of a BoNT epitope-containing composition. In some embodiments, the composition elicits an immune response directed to the BoNT epitope component of the composition.

In one embodiment, the present disclosure relates to a method of decreasing the likelihood of BoNT toxicity in a human or animal subject comprising: administering to the subject a therapeutically effective amount of a BoNT epitope-containing composition wherein the composition elicits an immune response directed to the BoNT epitope component of the composition. In another embodiment, the subject is administered a composition containing nucleic acids encoding BoNT epitopes.

In one embodiment, the present disclosure provides a method of eliciting an immune response in a human or animal subject comprising: administering to the subject a therapeutically effective amount of a BoNT epitope-containing composition wherein the composition elicits an immune response directed to the BoNT component of the composition.

In one embodiment, the present provides a composition for isolating, purifying, or detecting Receptor Associated Protein (RAP) comprising a polymer resin coupled to a plurality of peptides, wherein the peptides possess an affinity for specific binding to RAP.

In one embodiment, the present disclosure provides a method for isolating, purifying, or detecting RAP proteins, fragments, or derivatives thereof in a sample comprising: (a) contacting said sample with a polymer resin coupled to a plurality of peptides, wherein said peptides specifically bind to RAP, under conditions conducive to specific peptide-RAP binding; (b) removing non-specifically bound contaminants; (c) altering conditions to promote RAP release; and (d) recovering the released RAP.

In one embodiment, the present disclosure provides to a method of purifying anti-BoNT antibodies from a sample comprising: (a) contacting the sample with a polymer resin coupled to a fusion protein comprising a RAP carrier peptide and at least one real or mimetic BoNT epitope, under conditions conducive to specific epitope-antibody binding; (b) removing non-specifically bound contaminants; (c) altering conditions to release bound antibodies, and (d) recovering the released antibodies. In one embodiment, the BoNT epitopes are selected from the epitopes shown in FIG. 3 or Tables 3-5.

BRIEF DESCRIPTION OF THE FIGURES

FIG. 1. Real epitope map of BoNT/A light chain. The full-length BoNT/A sequence is shown in plain type. Four real epitopes were identified through screening of the BoNT/A peptide expression library with rabbit anti-BoNT/A antisera, designated Adel1, Adel2, Adel3, and Adel4. For each of Adel1, Adel2, and Adel4, multiple immunoreactive clones were isolated, designated-1, -2, etc. The real epitopes are defined as the region of overlap between the clones. FIG. 1 discloses SEQ ID NOS 92-101, respectively, in order of appearance.

FIG. 3. Alignment of BoNT real epitopes. Sequence of the del1, del2, del3, and del4 real epitopes is well conserved across the BoNT serotypes an in the related tetanus toxin. The Zn domain is the most highly conserved across the toxins. This region was not identified as a real epitope in the screening of BoNT/A-L and was used as a negative control for anti-BoNT blotting. These sequences were used to test the cross-reactivity of rabbit anti-sera FIG. 3 discloses SEQ ID NOS 102-133, respectively, in order of appearance.

FIG. 7. Amino Acid Sequences of Exemplary Fusion Proteins. Amino acid sequences of HisbioRAP (upper panel) and *C. perfringens* □-toxin (second panel) fusion proteins bearing three BoNT real epitope peptides in series. The del1 epitope of BoNT serotypes F, B, and A are highlighted. FIG. 7 discloses SEQ ID NOS 134-137, respectively, in order of appearance.

DETAILED DESCRIPTION

Figure 2:
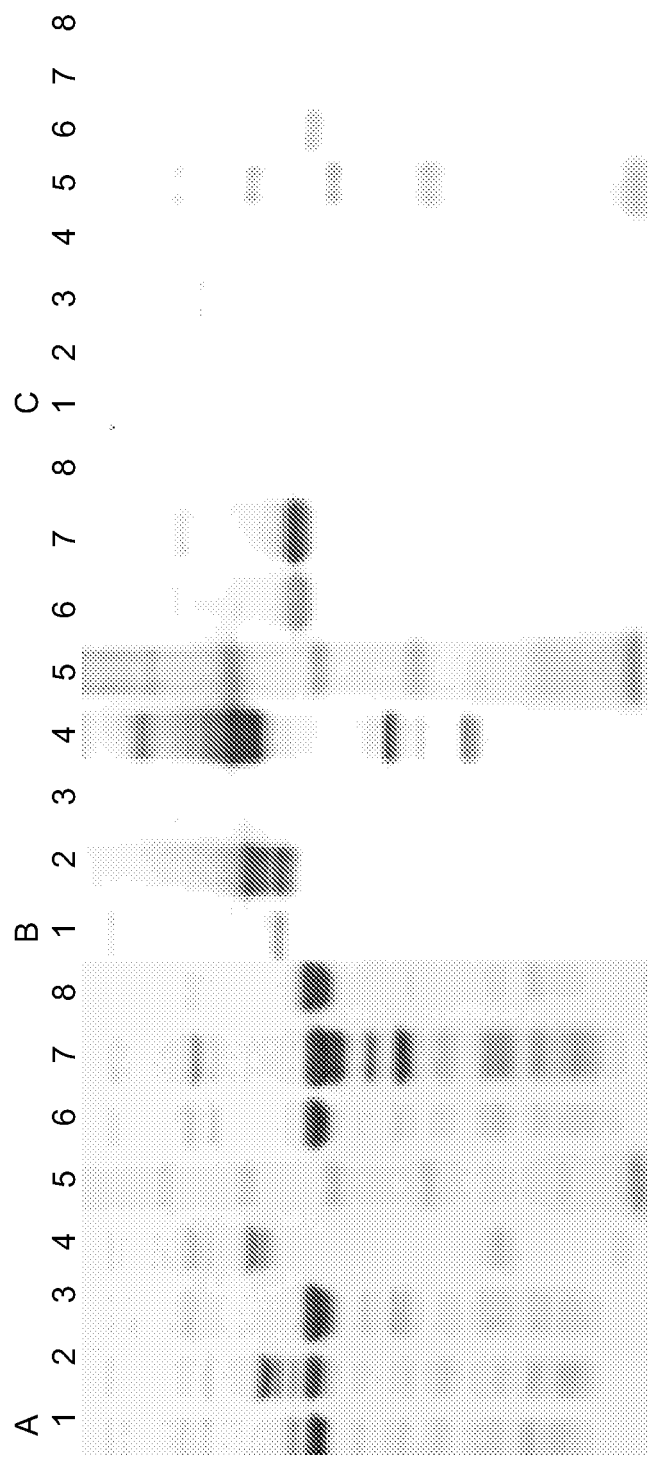
FIG. 2. Antigenic properties of identified BoNT/A real epitopes. Identified BoNT/A real epitopes were expressed in *E. coli* as HisbioRAP fusion proteins. Bacterial lysates were purified on Ni-Sepharose and the products resolved by SDS-PAGE. Proteins were visualized by Coomassie staining (A) and Western blotting (B-C). Blots were probed with rabbit anti-BoNT/A whole serum (B) or a fraction of the serum affinity purified, on HisbioRAP-del4-coupled resin. Samples were loaded in the following order: (1) BoNT/Adel2; (2) BoNT/Adel1-1(3) HisbioRAP control (4) BoNT/AB-L; (5) pre-stained molecular weight markers; (6) BoNT/Adel4; (7) BoNT/Adel1; (8) HisbioRAP-random peptide. BoNT/AB-L (lane 5) is a derivative of BoNT/A-L in which the BoNT/A-del4 region has been substituted with that of BoNT/B.

In practicing the present disclosure, many conventional techniques in cell biology, molecular biology, protein biochemistry, immunology, and bacteriology are used. These techniques are well-known in the art and are provided in any number of available publications, including *Current Protocols in Molecular Biology*, Vols. I-III, Ausubel, Ed, (1997); Sambrook et al., *Molecular Cloning: A Laboratory Manual*, Second Ed. (Cold Spring Harbor Laboratory Press, Cold Spring Harbor, N.Y., 1989).

Certain terms used herein are defined below. Unless defined otherwise, all technical and scientific terms used herein have the same general meaning as commonly understood by one skilled in the art.

As used herein, the singular forms "a," "an," and "the" include plural referents unless the content clearly indicates otherwise. For example, reference to "a cell" includes a combination of two or more cells, etc.

As used herein, "administration" of a composition to a subject includes any route of delivering the compound to the subject to perform its intended function. Administration can be carried out by any suitable route including oral, intranasal, parenteral (intravenous, intramuscular, intraperitoneal, or subcutaneous), or topical. Administration includes self-administration and administration by another.

As used herein, the terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encodes an antigen. The artisan will further understand that antigens are not limited to fall-length proteins, but can also include partial amino acid sequences. Moreover, sequences from different sources may be combined to generate mosaic antigens, depending on the specific intended use. In some embodiments, the mosaic antigen will include epitopes derived from different proteins. In some embodiments, the mosaic antigen will include epitopes derived from the same protein. The term "antigenic" is an adjectival reference to molecules having the properties of an antigen.

As used herein, the term "epitope" refers to that portion of a molecule that forms a site specifically recognized by an antibody or immune cell. A protein epitope may comprise amino acid residues directly involved in antibody binding, as well as residues not directly involved in binding that are nonetheless included in the antibody-epi tope footprint and excluded from the solvent surface. Epitopes may derive from a variety of physical characteristics of a protein, including primary, secondary, and tertiary amino acid structure, and amino acid/protein charge. Epitopes present within a molecule are referred to as "real epitopes." Real epitopes encompass wild-type sequences and variants of wild-type sequences. Real epitopes may exist within a wild-type protein, a naturally occurring variant of a wild-type protein, or an engineered variant of a wild-type protein. The term "mimetic epitope" refers to a molecule unrelated to a given real epitope that nonetheless specifically binds to antibodies that recognize the real epitope. Epitopes may be isolated, purified, or otherwise prepared by those skilled in the art. They may be obtained from natural sources including cells and tissues, or they may be isolated from host cells expressing a recombinant form of the epitope.

As used herein, "effective amount" refers to a quantity sufficient to achieve a desired effect. In the context of therapeutic or prophylactic applications, the effective amount will depend on the type and severity of the condition at issue and on the characteristics of the individual subject, such as general health, age, sex, body weight, and tolerance to pharmaceutical compositions. In the context of an antigenic composition, in some embodiments, an effective amount is an amount sufficient to result in a protective response against a pathogen. In other embodiments, an effective amount of an antigenic composition is an amount sufficient to result in antibody generation against the antigen. With respect to antigenic compositions, in some embodiments, an effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors. In the case of a biochemical application, in some embodiments, an effective amount will depend on the size and nature of the sample in question. It will also depend on the nature and sensitivity of the methods in use. The skilled artisan will be able to determine the effective amount based on these and other considerations.

As used herein, the term "polymer resin" refers to resins, such as, but not limited to polysaccharide polymers such as agarose and Sepharose™. The skilled artisan will understand that proteins may be covalently attached to the resin using methods well known in the art, including but not limited to cyanogen bromide activation, reductive animation of aldehydes, and the addition of iodoacetyl functional groups. The skilled artisan will further understand that functional equivalents of polysaccharide polymers may also be to immobilize proteins.

As used herein, the term "BoNT" refers to any of the seven serologically distinct botulinum neurotoxins produced by *Clostridium botulinum, Clostridium argentiensis*, and *Clostridium baratti*. Individual serotypes are referred to as BoNT/A, BoNT/B, BoNT/C, BoNT/D, BoNT/E, BoNT/F, and BoNT/G. Exemplary, non-limiting nucleic acid sequences of BoNT/A, /B, /C, /D, /E, /F, and /G are found in GenBank Accession numbers DQ409059, FM865705, AB200364, NZ ACSJ101000015, AM695754, X81714, and X74162, respectively. Exemplary, non-limiting amino acid sequences of BoNT/A, /B, /C, /D, /E, /F, and /G are found in GenBank Accession numbers ABD65472, CAR97779, BAD90572, ZP 04863672, CAM91137, CAA57358, and CAA52275, respectively. Exemplary, non-limiting nucleic and amino acid sequences of *C. tetani* tetanus toxin are found in GenBank Accession numbers AF154828 and AAF73267, respectively. As used herein, the term "BoNT/A-L" refers to the full-length botulinum neurotoxin A light chain. As used herein, the term "BoNT/B-L" refers to the full-length botulinum neurotoxin B light chain.

As used herein, the term "anti-BoNT antibody" refers to an antibody capable of specifically binding to BoNT. As used herein, an antibody includes a polyclonal antibody, a monoclonal antibody, and also refers to functional fragments (e.g., fragments which bind an antigen/epitope), such as Fv, Fab, Fc and CDRs.

As used herein, the term "carrier" or "carrier peptide" refers to a protein expressed as an in-frame fusion with a protein of interest to facilitate isolating, purifying, identifying or otherwise manipulating the protein or peptide of interest. The term encompasses proteins conventionally used as epitope tags, including but not limited to the receptor associated protein ("RAP"), Myc, green fluorescent protein ("GFP"), hemagglutinin ("HA"), FLAG, poly-histidine, thioredoxin, cholera toxin B subunit, *E. coli* cholera-like toxin, Halo-tag, and biotin. In some embodiments, the carrier comprises the combination of three tags comprising His-bio-RAP. The term also encompasses fragments or portions of these proteins, variant of these proteins, and peptides not conventionally used as epitope tags. The skilled artisan will understand that the term encompasses any proteins or peptides used to facilitate isolating, purifying, identifying, or otherwise manipulating a protein of interest.

As used herein, the term "*Clostridium perfringens* α-toxin" refers to *C. perfringens* phospholipase C. One exemplary α-toxin is shown by GenBank Accession number ABA64004.

As used herein, the term "Receptor Associated Protein (RAP)" *Homo sapiens* alpha-2-macroglobulin receptor-associated protein. One exemplary RAP protein is shown by GenBank Accession number AAA51553.

As used herein, the terms "immunogen" and "immunogenic" refer to molecules with the capacity to elicit an immune response. The response may involve antibody production or the activation of immune cells. The response may occur in vivo or in vitro. The skilled artisan will understand that a variety of macromolecule, including proteins, have the potential to be immunogenic. The skilled artisan will further understand that nucleic acids encoding a molecule capable of eliciting an immune response necessarily encodes an immunogen. The artisan will further understand that immunogens are not limited to full-length molecules, but may include partial amino acid sequences (e.g., epitopes). Moreover, sequences from different sources may be combined to generate mosaic immunogens, depending on the specific intended use.

As used herein, the terms "isolate" and "purify" refer to processes of obtaining a biological substance that is substantially free of material and/or contaminants normally found in its natural environment (e.g. from the cells or tissues from which a protein is derived, or substantially free from chemical precursors or other chemicals when chemically synthesized chemically.

As used herein, the term the terms "polypeptide," "peptide," and "protein" are used interchangeable to mean a polymer comprising two or more amino acids joined to each other by peptide bonds or modified peptide bonds (i.e., peptide isosteres). Polypeptides may include amino acids other than the naturally-occurring amino acids, as well as amino acid analogs and mimetics prepared by techniques that are well known in the art. The skilled artisan will understand that polypeptides, peptides, and proteins may be obtained in a variety of ways including isolation from cells and tissues expressing the protein endogenously, isolation from cell or tissues expressing a recombinant form of the molecule, or synthesized chemically.

As used herein, the term "sample" includes but is not limited to whole or fractionated prokaryotic or eukaryotic cells, whole or fractionated bodily tissue, whole or fractionated bodily fluid such as blood, lymph, mucus, tears, saliva, sputum, CSF, urine, or artificial bodily fluid. Samples also include stool, hair and/or sloughed cells.

As used herein, the term "subject" refers to a member of any vertebrate species. The methods of the presently disclosed subject matter are particularly useful for warm-blooded vertebrates. In some embodiments, the subject is avian and includes domestic (e.g., chicken, turkey) and wild bird species. In some embodiments, subjects include mammals such as humans, as well as those mammals of importance due to being endangered, of economic importance (animals raised on farms for consumption by humans) and/or social importance (animals kept as pets or in zoos) to humans. In particular embodiments, the subject is a human. In other embodiments, the subject is not human.

I. Epitopes

A. General

Disclosed herein are methods and compositions for the identification and isolation of polypeptide epitopes. In some embodiments, the epitopes are real epitopes. In other embodiments, the epitopes are mimetic epitopes. Mimetic epitopes are typically unrelated to a given real epitope but nonetheless specifically bind to antibodies that recognize the real epitope. In some embodiments, a mimetic epitope has a different amino acid sequence, secondary, tertiary and/or quaternary structure than a counterpart real epitope.

In some embodiments, epitopes are used singly, while in other embodiments, combinations of epitopes are used. Regarding combinations of epitopes, in some embodiments, the epitopes are presented as a collection of individual molecules for use; additionally, or alternatively, the combination of comprises a series of epitopes within a single polypeptide. In some embodiments, a combination of epitopes includes a variety of different real epitopes, a variety of different mimetic epitopes, or a combination of real and mimetic epitopes. Different epitopes used in combination include, but are not limited to, epitopes from different regions of a particular antigen and epitopes from different antigens. For example, in some embodiments, epitopes from different serotypes are combined; additionally or alternatively, in other embodiments, epitopes from different bacterial, fungal, viral, or other infectious agent are combined. By way of example, but not by way of limitation, in some embodiments, epitopes of 2, 3, 4, 5, 6 or 7 different serotypes BoNT are combined. Additionally, or alternatively, in some embodiments, epitopes for tetanus toxin, are combined with one or more BoNT serotype specific epitopes. In still other embodiments, epitopes for HIV and/or HCV, pneumonia are combined. The skilled artisan will understand that the disclosure is not limited to specific combinations of epi topes, and that any number of combinations of epitopes can be created to address a set of diseases or infections likely to occur together in a subject. By way of example, and not by way of limitation, the combination of epitopes can be administered to a subject to generate an immune response thereby preventing, treating, alleviating or decreasing the likelihood of disease or infection.

In some embodiments, a composition including multiple epitopes is provided. In some embodiments, each epitope is capable of individually eliciting an immune response in a human or animal subject. Additionally or alternatively, in some embodiments, administering a therapeutically effective amount of the composition to a subject elicits multiple immune responses directed to multiple epitopes. In some embodiments, each epitope specifically binds to an anti-BoNT antibody, and each epitope is capable of individually eliciting an immune response in a human or animal subject.

In some embodiments, the epitopes are linked to one or more carrier proteins, and in some embodiments, the carrier protein is used to aid in the identification, isolation and/or characterization of the epitopes. In some embodiments, the carrier protein is generally non-antigenic and/or non-immunogenic (e.g., it does not elicit a detectable immune response when administered to a subject). Additionally or alternatively, in some embodiments, the carrier protein enhances the solubility of the epitope; in other embodiments, the carrier protein facilitates excretion of the epitope from a cell (e.g., a host cell) and into the cell culture medium. In some embodiments, the epitope comprises a series of epitopes within a single polypeptide fused to a carrier protein.

In some embodiments, the epitopes are derived from botulinum neurotoxin, and in particular, from the botulinum neurotoxin light chains (BoNT). Exemplary BoNT real and mimetic epitopes are presented in FIG. 3 and Tables 3-5.

B. Methods of Generating and Identification of Real Epitopes

Real epitopes can be identified using bacterial expression systems well known in the art. For example, an expression library can be generated from a polynucleotide encoding the full-length protein. Random peptides derived from the full length protein can then be expressed in a host cell (e.g., *E. coli*) as fusion protein with a carrier. In some embodiments, carriers include one or more of a polyhistidine repeat (His), biotin (bio) and human Receptor Associated Protein (RAP). The carrier can be linked to the N-terminus or the C-terminus of the peptides. Bacterial colonies can then be replica plated and probed for recognition by an anti-antisera derived from the full-length protein. Immunoreactive peptides can then be sequenced and mapped to the full-length protein to identify real epitopes.

By way of example, but not by way of limitation, BoNT real epitopes (FIG. 3) were identified using a bacterial expression system well known in the art. An expression library was generated from a polynucleotide encoding the full-length BoNT/A light chain. The amino acid sequence of the BoNT/A light chain is shown in FIG. 1. Random peptides derived from the BoNT/A light chain were expressed in *E. coli* as fusion proteins bearing three N-terminal tags: a polyhistidine repeat (His), a biotinylatable peptide (bio), and human Receptor Associated Protein (RAP). Bacterial colonies were replica plated and probed for recognition by an anti-BoNT antisera. Immunoreactive peptides were sequenced and mapped to the light chain. The locations and sequences of the BoNT light chain real epitopes are given in FIG. 1.

C. Methods of Generating and Identification of Mimetic Epitopes

In some embodiments, mimetic epitopes are identified using phage display techniques well known in the art. For example, multiple random peptide display libraries are subjected to multiple rounds of bio-panning with an antibody specific for a molecule of interest. Immunoreactive particles can then be isolated and amplified.

Recombinant proteins encompassing the real and mimetic epitopes can be prepared using standard techniques well known in the art. For example, polynucleotides encoding carrier-epitope fusions can be cloned into plasmid vectors under the control of an inducible promoter and transformed into *E. coli*. Expression of the fusion protein construct can be induced under standard conditions and the fusion protein recovered from bacterial cell lysates using techniques routine in the art.

By way of example but not by way of limitation, BoNT mimetic epitopes were identified using phage display techniques well known in the art. Two random peptide display libraries were subjected to multiple rounds of biopanning with rabbit anti-BoNT antisera. Immunoreactive particles were isolated and amplified.

D. Methods of Expressing Epitopes and Preparing Antigenic Compositions

The present disclosure provides methods for preparing antigenic compositions, in some embodiments, the methods include transfecting or transforming a host cell with an expression vector encoding one or more epitopes, or one or more epitopes linked to a carrier protein, expressing the epitope or epitope fusion and isolating the epitope or epitope fusion so expressed. The skilled artisan will appreciate that a variety of tools and methods may be used to prepare compositions comprising real or mimetic epi topes. Any number of expression vectors may be used to produce fusion proteins. Exemplary vectors include, but are not limited to plasmid DNA vectors, viral vectors, bacterial vectors and mammalian vectors. Non-limiting examples of specific vectors known in the art include pUC, pET and Flexi vectors and derivatives thereof. In some embodiments, the fusion protein is encoded by a transposable element which integrates into a host genome.

Any number of carrier proteins may be used to facilitate expression, identification and manipulation of the fusion proteins, including but not limited to Myc, GFP, HA, FLAG, poly-histidine, thioredoxin, cholera toxin B subunit, *E. coli* cholera-like toxin, and Halo-tag and RAP.

Likewise, any number of bacterial or non-bacterial host cells may be used to express the proteins, including but not limited to bacteria such as *E. coli, Erwinia carotovora*, and *Bacillus subtilis*, eukaryotic cells such as yeast, plant, mammalian, and insect cells. Conventional molecular biology methods known in the art may be used to build the necessary constructs (e.g., expression vectors), including but not limited to PCR amplification of endogenous or recombinant DNA, direct cloning of endogenous DNA, oligonucleotide synthesis, or gene synthesis.

In addition, conventional biochemistry methods known in the art may be used to recover the fusion protein from bacterial or non-bacterial cell lysates. Cell-free translation systems may be used to generate the fusion protein and may be preferable under some circumstances. Examples of cell free translation systems include but are not limited to those that utilize reticulocyte lysate and wheat germ extracts. Detection of the epitope or related antibodies may be accomplished by a number of techniques, including but not limited to enzyme-linked immunoabsorbent assays (ELISA) and immunoblotting.

In some embodiments, an antigenic composition includes a fusion protein bearing a single real or mimetic epitope. In other embodiments, the antigenic compound comprises a fusion protein bearing multiple real or multiple mimetic epitopes. In yet another embodiment, the antigenic compound comprises a fusion protein bearing a combination of real and mimetic epitopes. Additionally or alternatively, in some embodiments, the antigenic compound includes multiple real and/or multiple mimetic epitopes derived from multiple pathogens.

In one embodiment, the fusion peptide is specifically recognized by an antibody known to bind the antigen from which the epitope was derived or modeled. In another embodiment, the real or mimetic epitope of the fusion peptide is capable of eliciting and immune response in a human or animal subject.

For example, in some embodiments, recombinant proteins encompassing BoNT real and mimetic epitopes can prepared using standard techniques well known in the art. Polynucleotides encoding carrier-BoNT fusions can be cloned into plasmid vectors under the control of an inducible promoter and transformed into a host cell such as *E. coli*. Expression of the fusion protein construct can be induced under standard conditions and the fusion protein recovered from bacterial cell lysates using techniques routine in the art. In some embodiments, the epitope includes one or more real or mimetic BoNT epitopes. Exemplary BoNT real and mimetic epitopes are presented in FIG. 3 and Tables 3-5.

In some embodiments, a method for producing an antigenic composition includes (a) expressing in a host cell a fusion protein comprising a carrier peptide and at least one epitope, wherein the carrier peptide is selected, from the group consisting of Receptor Associated Protein (RAP) and *Clostridium perfringens* α-toxin; and (b) isolating the fusion protein produced by the host. Additionally or alternatively, in some embodiments, the epitope includes a real or mimetic BoNT epitope. In some embodiments, the epitope is capable of eliciting an immune response in a human or animal subject. In some embodiments, the real or mimetic epitope is selected from the group consisting the epitopes shown in FIG. 3 and Tables 3-5. In some embodiments, the fusion protein is expressed in the host cell from an expression vector, and in some embodiments, the expression vector is selected from the group consisting of a plasmid DNA, a viral vector, a bacterial vector, a mammalian vector, and a vector capable of integrating into the genome of the host cell. Typically, the vector is capable of autonomous replication in a host cell. In some embodiments, the fusion protein includes a carrier peptide and multiple real and/or multiple mimetic BoNT epitopes, and in some embodiments, the real or mimetic epitopes are selected from the group consisting the epitopes shown in FIG. 3 and Tables 3-5.

II. Method for Isolating Fusion Proteins and RAP

A. RAP Fusions

Disclosed herein are methods and compositions useful for the isolation of RAP fusion proteins. In some embodiments, fusion of RAP, a RAP fragment or a RAP variant with a protein of interest enhances the solubility of the fusion protein, thereby facilitating isolation of the fusion via methods known in the art. For example, full-length RAP, the N-terminal half of RAP, and the C-terminal half of the RAP, can independently enhance the solubility of fusion peptides.

In the methods, a polypeptide of interest (e.g., one or more epitope) is fused to RAP, a RAP fragment, or RAP derivative or variant. The fusion protein is expressed in a host cell (e.g., in *E. coli*), wherein the RAP carrier protein enhances the aqueous solubility of the fusion protein. In one embodiment, the method includes the use of a RAP carrier peptide to enhance the solubility of any protein of interest.

In some embodiments, a RAP fusion protein comprising RAP, a RAP fragment or a RAP variant fused to a protein of interest, is affinity purified from a sample by contacting the sample with a heparin coupled to a polymer resin (RAP is a natural heparin ligand).

In some embodiments, the protein of interest is one or more real or mimetic BoNT epitopes. Exemplary BoNT real and mimetic epitopes are presented in FIG. 3 and Tables 3-5. Exemplary BoNT fusions are provided in FIG. 7.

For example, in some embodiments, a method is provide for isolating a real or mimetic BoNT epitope from a host cell comprising: expressing the epitope as a fusion protein with a Receptor Associated Protein (RAP) carrier peptide, wherein the carrier peptide enhances the solubility of said epitope; and isolating the fusion protein from solution. In some embodiments, the protein of interest is one or more real or mimetic BoNT epitopes. In some embodiments, the epitopes are selected from the BoNT real and mimetic epitopes presented in FIG. 3 and Tables 3-5. In some embodiments, the fusions are those shown in FIG. 7.

1. Isolation of RAP Proteins

In some embodiments, methods are provided for isolating, purifying, or detecting Receptor Associated Protein (RAP). In some embodiments, the methods include providing a polymer resin coupled to a plurality of peptides, wherein the peptides specifically bind to RAP.

In some embodiments, methods for isolating, purifying, or detecting Receptor Associated Protein (RAP) in a sample are provided. In some embodiments, the methods include: (a) contacting the sample with a polymer resin coupled to a plurality of peptides, wherein said peptides specifically bind to RAP, under conditions conducive to specific peptide-RAP binding; (b) removing non-specifically bound contaminants; (c) altering conditions to promote RAP release; and (d) recovering the released RAP.

In some embodiments, the plurality of peptides includes RAP-binding peptides isolated by phage display. In some embodiments, the plurality of peptides include the peptides listed in Table 6. In some embodiments, heparin is coupled to the resin.

B. Other Fusions

In some embodiments, the fusion protein includes a carrier or tag protein other than RAP. By way of example, but not by way of limitation, the carrier protein may include one or more of conventionally used as epitope tags such as Myc, GFP, HA, FLAG, poly-histidine, thioredoxin, cholera toxin B subunit, *E. coli* cholera-like toxin, Halo-tag, and biotin. In some embodiments, the carrier comprises the combination of three tags comprising His-bio-RAP. In some embodiments, purification methods include the use of nickel-binding peptides shown in Table 7. In some embodiments, purification methods may include the use of streptavidin and/or Strep A coupled to a polymer resin for use in affinity chromatography. In some embodiments, purification methods include the use of streptavidin-binding peptides shown in Table 8.

In some embodiments, the protein of interest is one or more real or mimetic BoNT epitopes. Exemplary BoNT real and mimetic epitopes are presented in FIG. 3 and Tables 3-5. Exemplary multiple epitope fusions are shown in FIG. 7.

III. Method for Isolating *C. perfringens* α-Toxin Fusion Proteins *E. coli*

Disclosed herein are methods and compositions useful for the isolation of *C. perfringens* α-toxin fusion proteins. In some embodiments, the fusion includes α-toxin, an α-toxin fragment, or an α-toxin derivative or variant, and at least one fusion partner. In some embodiments, the fusion partner is one or more epitopes. In general, the methods include expressing the α-toxin fusion in *E. coli*, wherein the α-toxin carrier protein promotes secretion of the fusion protein into the culture medium. In one embodiment, α-toxin carrier peptide is used to promote the secretion of a fusion protein into a bacterial culture medium, thereby facilitating isolation of the fusion protein.

In some embodiments, the fusion partner is one or more real or mimetic BoNT epitopes. Exemplary BoNT real and mimetic epitopes are presented in FIG. 3 and Tables 3-5.

In some embodiments, a method is provided for isolating a real or mimetic BoNT epitope from host cell comprising: expressing the epitope as a fusion protein with a *Clostridium perfringens* α-toxin carrier peptide, wherein the fusion protein is secreted by *E. coli* into the culture medium; and isolating the fusion protein from the culture medium. In some embodiments, the epitopes are selected from the BoNT real and mimetic epitopes presented in FIG. 3 and Tables 3-5. In some embodiments, the fusions are those shown in FIG. 7.

IV. Methods for Isolating, Purifying, or Detecting Antibodies

In one embodiment, the present disclosure provides methods for isolating or purifying antibodies in a sample. In some embodiments, the method comprises contacting the sample with a biochemically effective amount of a composition comprising one or more real and/or mimetic epitopes under conditions conducive to specific antibody-antigen binding, providing a wash step in which non-specifically bound contaminants are removed, altering conditions to promote the release of bound antibodies, and recovering released antibodies. In some embodiments the sample comprises a cell, tissue, bodily fluid, or fraction thereof. In some embodiments the sample comprises an experimental sample. In some embodiments, experimental samples comprise lysates from cultured cells or fractions thereof tissue homogenates and/or bodily fluids, etc. from experimental animals or fractions thereof. In other embodiments the sample comprises a patient sample.

In some embodiments, the antibodies are BoNT antibodies and the epitope comprises one or more real or mimetic BoNT epitopes. In some embodiments, the BoNT epitope is selected, from the epitopes of FIG. 3 and Tables 3-5. Additionally or alternatively, in some embodiments, the BoNT epitope is present as a fusion with a carrier protein.

In some embodiments, the methods related to the detection and/or quantification of antibodies in a sample comprising contacting a sample with a biochemically effective amount of a composition comprising a real or mimetic epitope under conditions conducive to specific antibody-antigen binding, providing a wash step in which non-specifically bound contaminants are removed, and detecting the presence and/or amount of bound antibody. In some embodiments, the methods encompass the use of secondary detection reagents including but not limited to species-specific secondary antibodies coupled, to a fluorescent or enzymatic label. In some embodiments the sample comprises a cell, tissue, or bodily fluid or fraction thereof. In some embodiments the sample comprises an experimental sample. In some embodiments, experimental samples comprise lysates from cultured cells or fractions thereof, tissue homogenates and/or bodily fluids, etc. from experimental animals or fractions thereof. In other embodiments the sample comprises a patient sample.

In some embodiments, the antibodies are BoNT antibodies and the epitope comprises one or more real or mimetic BoNT epitopes. In some embodiments, the BoNT epitope is selected, from the epitopes of FIG. 3 and Tables 3-5. Additionally or alternatively, in some embodiments, the BoNT epitope is present as a fusion with a carrier protein.

In some embodiments, methods are provided for isolating or purifying anti-BoNT antibodies from a sample comprising: (a) contacting the sample with a biochemically effective amount of the composition comprising at least one BoNT epitope under conditions conducive to specific epitope-antibody binding; (b) removing non-specifically bound contaminants; (c) altering conditions to release bound antibodies; and (d) recovering the released antibodies.

In further embodiments, methods are provided for detecting, the presence of anti-BoNT antibodies in a sample comprising: (a) contacting the sample with a diagnostically effective amount of the composition comprising at least one BoNT epitope under conditions conducive to specific epitope-antibody binding, and (b) detecting the antibodies. In some embodiments, the BoNT epitope is selected, from the epitopes of FIG. 3 and Tables 3-5. Additionally, or alternatively, in some embodiments, the BoNT epitope is present as a fusion with a carrier protein.

In some embodiments, methods are provided for purifying anti-BoNT antibodies from a sample comprising: (a) contacting the sample with a polymer resin coupled to a fusion protein comprising a RAP carrier peptide and at least one real or mimetic BoNT epitope, under conditions conducive to specific epitope-antibody binding; (b) removing non-specifically bound contaminants; (c) altering conditions to release bound antibodies, and (d) recovering the released antibodies. In some embodiments, the BoNT epitope is selected from the epitopes of FIG. 3 and Tables 3-5. Additionally, or alternatively, in some embodiments, the BoNT epitope is present as a fusion with a carrier protein.

V. Method of Diagnosing

In some embodiments, the methods relate to diagnosing the exposure of a human or animal subject to a pathogen, comprising detecting the presence of antibodies that specifically bind the pathogen, in a sample derived from the subject. For example, in some embodiments, the method encompasses contacting the sample with a polymer resin coupled to a fusion protein, comprising one or more carrier proteins (e.g., RAP) and one or more real or mimetic epitopes under conditions conducive to specific antibody-antigen binding, providing a wash step to remove non-specifically bound contaminants, altering conditions to release bound antibodies, and recovering released, antibodies, in other embodiments, the fusion protein is linked to a solid support and enzyme-linked immunosorbent assay is used to detect the antibodies. For example, in one embodiment, the sample is contacted with the fusion protein linked to the solid support under conditions conducive to specific antibody-antigen binding, a wash step is provided to remove non-specifically bound contaminants, and a second fusion protein is provided to identify the bound antibody. In some embodiments, secondary reagents are used to aid in the identification and/or quantification of the bound antibody.

In some embodiments, the pathogen comprises one or more of *Clostridium botulinum*, *Clostridium argentiensis*, and *Clostridium baratti*, and the RAP fusion comprises RAP, a RAP fragment or RAP variant fused to one or more real or mimetic BoNT epitopes. Exemplary BoNT real and mimetic epitopes are presented in FIG. 3 and Tables 3-5.

In some embodiments, methods are provided for diagnosing the exposure of a human or animal subject to BoNT comprising: (a) contacting a biological sample from the subject with a diagnostically effective amount of the composition comprising at least one BoNT epitope, under conditions conducive to specific epitope-antibody binding, and (b) contacting the sample with an appropriate secondary detection reagent. In some embodiments, the sample is a cell, tissue, or bodily fluid. In some embodiments, the BoNT epitope is selected from the epitopes of FIG. 3 and Tables 3-5. Additionally or alternatively, in some embodiments, the BoNT epitope is present as a fusion with a carrier protein.

VI. Methods of Eliciting an Immune Response in a Human or Animal Subject

The present disclosure provides methods for eliciting an immune response in a human or animal subject comprising administering to the subject a therapeutically effective amount of a composition comprising a real or mimetic epitope, wherein the composition elicits an immune response directed to the epitope. In some embodiments, the antigenic composition comprises a fusion protein bearing a single real or mimetic epitope. In another embodiment, the antigenic composition comprises a fusion protein bearing multiple real or multiple mimetic epitopes. In yet another embodiment, the antigenic composition comprises a fusion protein bearing a combination of real and mimetic epitopes. Additionally or alternatively, in some embodiments, the antigenic composition includes multiple real or multiple mimetic epitopes derived from multiple pathogens. In another embodiment, the antigenic composition includes a combination of real and mimetic epitopes derived from multiple pathogens.

In some embodiments, the methods include immunizing a human or animal subject against BoNT toxicity. Additionally or alternatively, in some embodiments, the methods further include decreasing the likelihood or severity of BoNT toxicity in a human or animal subject.

In some embodiments, the animal to be immunized includes livestock, such as animals used for human consumption. In some embodiments, the animal includes domestic birds (e.g., chickens, turkeys) or wild birds. In other embodiments, the animal to be vaccinated includes cattle, sheep, goats, pigs, dogs and cats. In other embodiments, the animal to be vaccinated does not include humans. In alternative embodiments, the animal to be vaccinated is a human.

In some embodiments, methods of immunizing a human or animal subject against BoNT toxicity are provided. In some embodiments, the methods include administering to the subject a therapeutically effective amount of the composition comprising at least one BoNT epitope, wherein the composition elicits an immune response directed to the BoNT component of the composition. In some embodiments, the BoNT epitope is selected from the epitopes of FIG. 3 and Tables 3-5. Additionally or alternatively, in some embodiments, the BoNT epitope is present as a fusion with a carrier protein.

In some embodiments, method of decreasing the likelihood of BoNT toxicity in a human or animal subject are provided. In some embodiments, the methods include administering to the subject a therapeutically effective amount of a composition comprising at least one BoNT epitope, wherein the composition elicits an immune response directed to the BoNT component of the composition. In some embodiments, the BoNT epitope is selected, from the epitopes of FIG. 3 and Tables 3-5. Additionally or alternatively, in some embodiments, the BoNT epitope is present as a fusion with a carrier protein.

In some embodiments, a method of eliciting an immune response in a human or animal subject is provided. In some embodiments, the method includes administering to the subject a therapeutically effective amount of the composition comprising at least one BoNT epitope, wherein the composition elicits an immune response directed to the BoNT component of the composition. In some embodiments, the BoNT epitope is selected from the epitopes of FIG. 3 and Tables 3-5. Additionally or alternatively, in some embodiments, the BoNT epitope is present as a fusion with a carrier protein.

A. Pharmaceutical Compositions Including One or More Real or Mimetic Epitopes

Disclosed herein are pharmaceutical compositions including one or more real or mimetic epitopes, useful for eliciting an immune response. Pharmaceutical compositions are typically formulated to be compatible with its intended route of administration. Examples of routes of administration include parenteral (e.g., intravenous, intradermal, intraperitoneal or subcutaneous, oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., multiple days of treatment).

Pharmaceutical compositions suitable for injectable use can include sterile aqueous solutions (where the components are water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

Oral compositions generally include an inert diluent or an edible carrier. For the purpose of oral therapeutic administration, the active compound can be incorporated with excipients and used in the form of tablets, troches, or capsules. e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer.

B. Dosage of Pharmaceutical Composition Including One or More Real or Mimetic Epitopes Dosage, toxicity and therapeutic efficacy of epitope-containing compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of an epitope sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's antibody titer.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described, herein can include a single treatment or a series of treatments.

VII. Method for Isolating Real or Mimetic RAP Binding Partners

In further embodiments, RAP, a RAP fragment or a RAP variant is coupled to a polymer resin and is used to isolate real or mimetic RAP binding partners generated by phage display. In some embodiments, the bound, real or mimetic RAP binding partner is eluted with heparin.

EXAMPLES

The present invention is further illustrated by the following examples, which should not be construed as limiting in any way, Materials and Methods Cells and Plasmids—

Recombinant DNAs were cloned and amplified using *E. coli* DH5αF' cells. Fusion proteins were expressed in *E. coli* BL21(λDE3) cells. Plasmid pUCentryBoNT/A-L1 (unpublished) was used to generate the BoNT/A library. The plasmid carries the BoNT/A light chain coding sequence flanked by unique KpnI and XbaI sites on the 5' end, and unique SalI and SacI sites on the 3' end (5'-KpnI-XbaI-BoNT/A-L-SalI-SacI-3'). Fusion proteins bearing BoNT real or mimetic epitopes were expressed in plasmid pParaBAD-T7HisbioRAP2 (unpublished) under the control of a bacteriophage T7 promoter. Plasmid pETαtoxABglII1 (unpublished) encodes the *C. perfringens* α-toxin under the control of a bacteriophage T7 promoter. All vectors were constructed to carry similar polylinkers to allow for ease of subcloning.

Enzymes—

Restriction enzymes, T4 DNA-polymerase, S1 nuclease and rapid DNA ligation kits, were purchased from Fermentas Life Sciences.

Oligonucleotides—

Complementary oligonucleotide pairs encoding BoNT real epitopes are listed in Table 1. All were synthesized at GenScript Corporation. Fusion proteins bearing epitopes derived from these oligos were given "s" (synthetic) designation (Adel1s, Adel4s, Bdel1s, Fdel1s). Oligos were also used to generate mosaic peptides carrying multiple real epitopes in series (BA-del1s, FA-del1s, FBA-del1s).

Antibodies—

Rabbit antisera raised against BoNT/A, /B and /F were kindly provided by Dr. Vertiev (Russia). Purified rabbit anti-BoNT antibodies were purchased from Metabiologics Inc (Madison, Wis.).

Generation of a BoNT/A Expression Library—

Plasmid pUCentryBoNT/A-L1 was cut with KpnI and XbaI. Digestion with XbaI generated a 5' overhang susceptible to degradation by Exonuclease III. Digestion with KpnI generated a 3' overhang resistant to degradation by Exonuclease III. To generate a series of 5' BoNT/A deletions, the linearized pUCentryBoNT/A-L1 was treated sequentially with Exonuclease III, S1 nuclease, and DNA ligase. To generate a series of 3' cutbacks, the 5' deletion library was digested with SalI and SacI, and then treated sequentially with Exonuclease III, S1 nuclease, and DNA ligase. The cutbacks were excised as EcoRI-XhoI fragments, isolated by gel electrophoresis, and subcloned into pParaBAD-Hisbio-RAP. The library consisted of $3 \times 10^4$ independent clones with an average BoNT/A fragment length of 75 base-pairs.

Screening of the BoNT/A Expression Library—

The BoNT expression library was grown on LB-agar plates supplemented with ampicillin. Colonies were replica plated and transferred to nitrocellulose for immunoblotting using methods standard in the art. Colonies were probed with rabbit anti-BoNT/A and an anti-rabbit HRP secondary antibody. Immunoreactivity was visualized with metal-enhanced DAB (Pierce).

Expression and Purification of Recombinant Proteins—

All bacterial cultures were grown at 37° C. to an absorbency of 0.5-0.6 (600 nm). Protein expression was induced by addition of isopropyl-β-D thiogalactoside. HisbioRAP cultures were transferred to 24° C. and induced for 16 hours. Bacteria were lysed by sonication and the recombinant proteins purified from the soluble fraction by affinity chromatography using Ni-NTA Superflow (Qiagen). Cultures expressing the α-toxin-BoNT/FRA-del1 fusion were induced for 90 minutes at 37° C. The fusion protein was purified from the culture media by ultrafiltration on PREP/SCALE-TFF Cartridge 30K (Millipore) and ion-exchange chromatography on HiTrap™ QFF (GE Healthcare).

Immunization BoNT Real Epitopes—

Six-to-eight-week-old female BALB/c mice were purchased from Harlan Laboratories, Inc. Mice were allowed a 1-week period of acclimatization and then vaccinated intraperitoneally or subcutaneously with HisbioRAP-BoNT/FBA-del1s (FIG. 7), formaldehyde-treated α-Tox-FBA-del1s (FIG. 7), or control in the presence of Freunds Complete and Freunds Incomplete adjuvants. Three rounds of immunization were performed two weeks apart with 10, 20 and 40 μg of antigen, respectively. Tail bleeds were drawn at 28 and 42 days post-immunization and screened by ELISA. Results are presented as fold increase in $OD_{450}$ over pre-immune sera (Table 2).

Immunization with BoNT Mimetic Epitopes

Six-to-eight-week-old female BALB/c mice were purchased from Harlan Laboratories, Inc. Mice were allowed a 1-week period of acclimatization and then vaccinated intraperitoneally with 25 mg of HisbioRAP-BoNT/A-mimetic-8 at weeks 1, 3, and 4. The HisbioRAP-BoNT/A-mimetic-8 fusion protein bears eight BoNT/A mimetic epitopes in series: BoNT/AVII1-3, BoNT/AVII1-6, BoNT/AVII1-13, BoNT/AVII1-19, BoNT/AVII1-20, BoNT/AVII3-17, BoNT/AVII5-4, BoNT/AVII5-18 (shown in Table 3). Control mice were immunized with normal saline only. At week 5, mice were challenged with a dose of BoNT/A corresponding to 5× the LD50.

ELISA—

Diluted mouse sera were added to ELISA wells coated with α-Tox-FBAdel1s or HisbioRAP-FRAdel1s. Plates were incubated at 37° C. for 60 minutes, washed, and probed with goat anti-mouse HRP (Accurate Chemical) for 45 min at 37° C. Following a final wash, 200 μl of tetramethyl benzidine substrate was added to each well and incubated for 20 minutes. The reaction was terminated by the addition of $H_2SO_4$ to a final concentration of 0.2 N. Absorption was measured at 450 nm.

Western Blot—

Proteins were resolved on 4-10% SDS-PAGE gradient gels and transferred to PVDF (Millipore). Membranes were blocked with PBS, 0.1% Tween 20, 2% BSA and incubated with specified primary antibodies. Membranes were then probed with species-specific antibodies coupled to HRP and developed with metal enhanced DAB (Pierce).

Phage Display—

Phage display library Ph.D.-12™ (New England Biolabs) and phage display library MD12™ (Alpha Universe LLC) were used to isolate BoNT mimetic epitopes. Both libraries utilize filamentous phage M13 as a peptide carrier. Ph.D.-12™ peptides are exposed to the surface of the phage particle as fusion of protein III. MD12™ peptides are exposed as a fusion of protein VII.

BoNT mimetic epitopes were isolated from a random peptide display library using a modified biopanning protocol. Conventional biopanning utilizes a representative pool of recombinant particles (phages, cells or ribosomes), each member of which expresses a single species of fusion protein. The pool is incubated with an immobilized target molecule, and non-binding particles are washed away. Bound particles are then eluted and amplified. After several rounds of selection, even very rare binding events can be isolated and amplified.

In the modified protocol, a depletion step was included in which the peptide display library was incubated with pre-Immune rabbit sera. Non-specific antibody-display particle complexes were removed with Staphylococcal protein A and Streptococcal protein G. This step depleted the display library of non-specific interactors and ensured that probing the library with anti-BoNT antisera would yield only specific interactions. Following the depletion step, the display library was subjected to three rounds of biopanning with anti-BoNT targets. Random peptide libraries of BoNT/A, BoNT/B, and BoNT/E were screened with anti-BoNT/A, anti-BoNT/B, and anti-BoNT/E antisera, respectively.

Example 1

Identification of Real BoNT Epitopes

The BoNT/A expression library was screened for immunoreactivity with rabbit anti-BoNT/A (See Materials and Methods, supra). Four antigenic regions of the BoNT/A light chain were identified, designated real epitopes Adel1, Adel2, Adel3, and Adel4 (FIG. 1). Multiple positive clones were isolated for the del1, del2 and del4 regions, designated-1-2, etc. Analysis of the clones showed the real epitope to be the region of overlap (FIG. 1).

HisBioRAP fusion proteins bearing Adel1, Adel2, and Adel4 peptides were probed by western blot with anti-BoNT/A serum (FIG. 2B). A full-length serotype A/B hybrid (BoNT/AB-L) and the HisbioRAP carrier peptide were loaded as positive and negative controls, respectively. BoNT/AB-L is a derivative of BoNT/A-L, in which the Adel4 epitope has been substituted with that of BoNT serotype B (BoNT/B). Protein resolution was confirmed by Coomassie staining (FIG. 2A) and an identical blot was probed with the antiserum.

All BoNT derived fusions were detected by BoNT/A antisera, while the HisbioRap carrier protein was not (FIG. 2B). Thus, recognition of the BoNT/A fusion proteins by anti-BoNT/A antibodies is specific for the BoNT component of the proteins, and not the HisbioRAP carrier peptide.

While the native Adel3 epitope shows immunoreactivity with anti-BoNT/A serum (as in expression library screening), it is not reactive by Western blot (not shown). This suggests that unlike Adel1, Adel2, and Adel4, Adel3 likely encodes a structural epitope that does not withstand treatment with SDS. Detection of the Adel1, Adel2, and Adel4 peptides by western blot suggests that they generate linear epitopes.

Example 2

Isolation of Anti-BoNT/A Antibodies Specific for the Adel4 Epitope

HisbioRAP fusion proteins bearing Adel1, Adel2, and Adel4 peptides were probed by western blot with anti-BoNT/A serum purified against a HisbioRAP-BoNT/Adel4s fusion protein (FIG. 2C). BoNT/AB-L and the HisbioRAP carrier peptide were loaded as negative controls. Protein resolution was confirmed by Coomassie staining (FIG. 2A) and an identical blot was probed with the purified serum (FIG. 2C).

Of the BoNT-derived proteins loaded, only that bearing the Adel4 epitope was detected by the purified serum (FIG. 2C, lane 6). None of the other BoNT/A real epitopes were detected, nor was the full-length BoNT/AB-L hybrid (FIG. 2C).

These results illustrate several points. First, recombinant fusion proteins bearing BoNT real epitopes are effective tools for isolating anti-BoNT antibodies from whole serum. Second, BoNT epitopes within a given serotype are distinct from one another, with differing antibody specificities. For example, purified anti-Adel4 did not recognize Adel1 or Adel2 (FIG. 2C). Third, although the BoNT real epitopes are well conserved across the BoNT serotypes (FIG. 3), at least some are sufficiently distinct from one another to display differing antibody specificities. For example, purified anti-Adel4 did not recognize the Bdel4 epitope of the BoNT/AB-L fusion (FIG. 2C).

Example 3

Cross-Reactivity of BoNT Antisera with the BoNT/A, /B, and F/del1 Epitopes

HisbioRAP fusion proteins bearing the Adel1, Bdel1, and Fdel1 epitopes singly or in combination were probed by Western blot with rabbit antisera raised against BoNT/A, BoNT/B, or BoNT/F (FIG. 4B-D). BoNT/A-Zn was loaded as a negative control. Protein resolution was confirmed by Coomassie staining (FIG. 4A) and identical blots were probed with each antisera.

Each of the antisera tested demonstrated serotype specificity. Anti-BoNT/A recognized the Adel1 epitope when present singly, in combination with Bdel1 and Fdel1, and in the context of the full-length BoNT/AB-L hybrid protein (FIG. 4D). Anti-BoNT/A did not recognize the Bdel1 or Fdel1 epitopes (FIG. 4D). Anti-BoNT/B showed a similar degree of specificity, recognizing the Bdel1 epitope when present singly, in combination with the Adel1 and Fdel1 epitopes, and in the context of the full-length BoNT/AB-L hybrid protein (FIG. 4C). Anti-BoNT/B did not recognize the Adel1 or Fdel1 epitopes (FIG. 4C). Anti-BoNT/F recognized the Fdel1 epitope when present singly, in combination with the Adel1 and Bdel1 epitopes, and in the context of the full-length BoNT/AB-L hybrid protein (FIG. 4B). However, while anti-BoNT/F did not recognize the Adel1 epitope, it did recognize Bdel1. Although anti-BoNT/F showed somewhat less specificity than anti-BoNT/A and BoNT/B, all showed some degree of serotype specificity.

Thus, although the sequence of the BoNT real epitopes are well conserved across the serotypes, they are sufficiently distinct from one another to display differing antibody specificities. BoNT del1 peptides may be used for characterizing, diagnosing, or otherwise distinguishing between BoNT serotypes.

Example 4

Immunogenic Properties of a BoNT Mosaic Antigen

BALB/c mice were vaccinated with fusion proteins carrying multiple BoNT real epitopes, so-called mosaic antigens. Animals were injected with HisbioRAP-BoNT/FBAdel1s (FIG. 7, upper panel) or α-Tox/FBAdel1s (FIG. 7, second panel) over a period, of 4 weeks, and screened for an immune response at 28 and 42 days by direct ELISA.

Immunization with α-Tox/FBAdel1s resulted in a 4-15 fold increase in recognition of the immunogen as compared to pre-immune sera (Table 2). Immunization with HisbioRAP-FBAdel1s resulted in a 30-33 fold increase in recognition of the immunogen as compared to pre-immune sera (Table 2).

Example 5

Serotype Specificity of Anti-BoNT/FBAdel1

Figure 4:
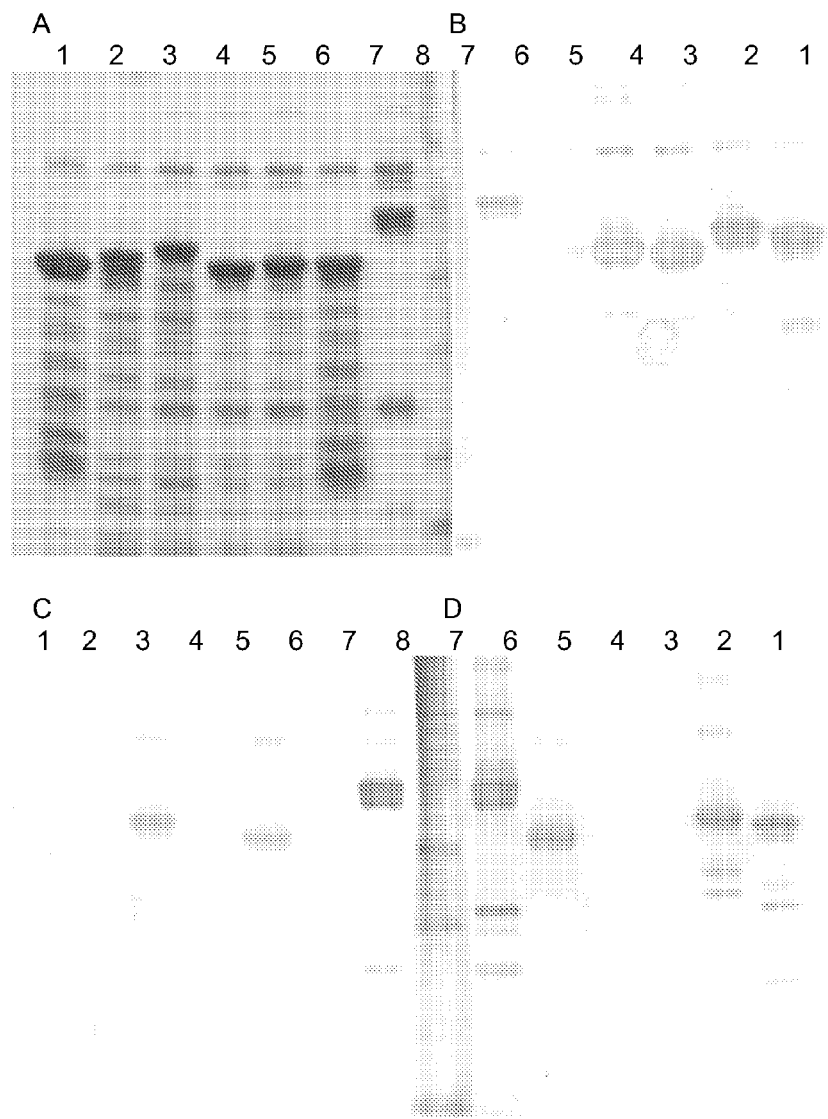
FIG. 4. Cross-reactivity of BoNT antisera with the BoNT/A, /B, and /F del1 epitopes BoNT/A, /B, and /F del1 peptides were expressed in *E. coli* as HisbioRAP fusion proteins. Bacterial lysates were purified on Ni-Sepharose and the products resolved by SDS-PAGE. Proteins were visualized by Coomassie staining (A) and Western blotting (B-D). Blots were probed with rabbit anti-BoNT/F (B), anti-BoNT/B (C), or anti-BoNT/A (D). Samples were loaded in the following order: (1) BoNT/A-Zn; (2) BoNT/FAdel1; (3) BoNT/BAdel1; (4) BoNT/Fdel1; (5) BoNT/Bdel1; (6) BoNT/Adel1, (7) BoNT/AB-L; (8) pre-stained molecular markers, BoNT/AB-L is a BoNT/A-L derivative in which the C-terminal region has been substituted with the corresponding region of BoNT/B-L.

As demonstrated in FIGS. 2-4, real epitopes described herein are immunogenic when introduced into a host in the context of the full-length toxin. It is for this reason that antisera raised against BoNT/A, /B, and /F recognize fusion proteins bearing the isolated epitopes. To demonstrate that the epitopes are immunogenic in the context of a fusion protein, a series of BoNT-derived fusions were probed by Western blot with anti-BoNT/A or /B antisera (FIG. 5B-C), or with mouse antisera raised against α-Tox/FBAdel1s, a fusion protein bearing the Adel1, Bdel1, and Fdel1 epitopes (FIG. 7, second panel). BoNT/A-L, BoNT/B-L, and HisbioRAP-BoNT/FBAdel1 were loaded as positive controls. A GFP-BoNT/A-CH fusion was also loaded as a positive control for anti-BoNT/A. HisbioRAP-BoNT-Zn was included as a negative control. Protein resolution was confirmed by Coomassie staining (FIG. 5A) and identical blots were probed with antisera.

Figure 5:
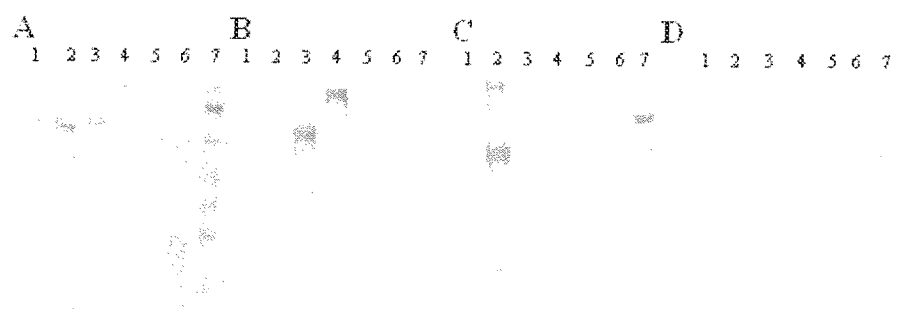
FIG. 5 Cross-reactivity of anti-BoNT antibodies raised against a BoNT/FBAdel1 mosaic peptide. BoNT/B-L, /A-L, /A-CH, /A-Zn, and /FBAdel1 peptides were expressed in *E. coli* as HisbioRAP fusion proteins. Bacterial lysates were purified on Ni-Sepharose and the products resolved by SDS-PAGE. Proteins were visualized by Coomassie staining (A) and Western blotting (B-D). Blots were probed with rabbit anti-BoNT/A (B), anti-BoNT/B (C), or the sera of mice immunized with a BoNT/FBAdel1 peptide, Samples were loaded in the following order: (1) tetanus toxin light chain; (2) BoNT/B-L; (3) BoNT/A-L; (4) GFP-BoNT/A-CH; (5) BoNT/A-Zn; (6) BoNT/FBAdel1; (7) pre-stained molecular weight markers.

Anti-BoNT/A recognized full-length BoNT/A, BoNT/A-CH, and the FBAdel1 fusion protein, but did not recognize full-length BoNT-L (FIG. 5B). Anti-BoNT/B showed similar specificity, recognizing full-length BoNT/B-L and the FBAdel1 fusion, but not BoNT/A-L or BoNT/A-CH (FIG. 5C). Both of these findings are consistent with the high degree of serotype specificity of these antisera demonstrated in FIG. 4. Notably, neither anti-BoNT/A nor anti-BoNT/B recognized tetanus toxin light chain (FIG. 5B-C), despite the fact that it bears a well conserved del1 epitope (FIG. 3). Conversely, the anti-FBAdel1 antisera recognized not only BoNT-A-L, BoNT/B-L, and FBAdel1, it also recognized tetanus toxin light chain (FIG. 5 D) and BoNT/G-L (not shown).

These findings demonstrate several important points. First, the BoNT real epitopes described herein elicit immune responses even when outside the context of the full-length toxin and in the context of a fusion protein. Second, mosaic antigens bearing multiple BoNT real epitopes elicit multiple independent immune responses. Thus, anti-FBAdel1 shows immunoreactivity to BoNT/A-L (FIG. 5B), BoNT/B-L (FIG. 5C), and BoNT/G (not shown). Third, mosaic antigens bearing multiple BoNT real epitopes are more potent immunogens than the full-length toxins, generating a profile of anti-BoNT antibodies that no longer display a high degree of serotype specificity. Thus, anti-FBAdel1 shows immunoreactivity with tetanus toxin whereas anti-BoNT/A and anti-BoNT/B do not.

Example 6

Identification of BoNT Mimetic Epitopes Phage Display

BoNT/A, BoNT/B, and BoNT/E epitope mimetics were isolated from a random peptide display library using a modified biopanning protocol (See Materials and Methods, supra). Twenty-two BoNT/A mimetics were isolated as fusions with phage capsid protein III and VII (Table 3). Seventeen BoNT/B mimetics were isolated as fusions with protein (Table 4). Thirteen BoNT/E mimetics were isolated as fusions with phage capsid protein VII (Table 5).

Example 7

Purification of Anti-BoNT Antibodies with BoNT Mimetic Epitopes

Figure 6:
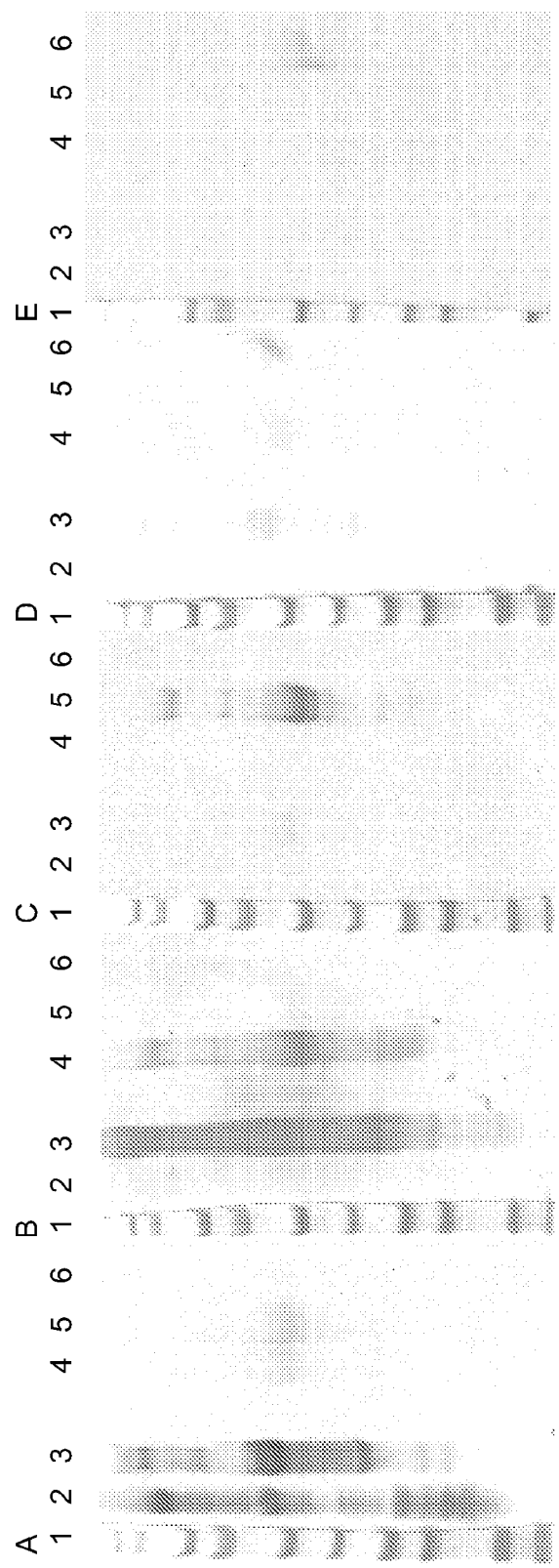
FIG. 6. Use of mimetic BoNT epitopes to affinity purify anti-BoNT/A antibodies. BoNT/A heavy and light chains were expressed in *E. coli*. BoNT mimetic epitopes AIII-1, AIII-L1, and AIII-26 were expressed in *E. coli* as HisbioRAF fusion proteins. Bacterial extracts were resolved by SDS-PAGE and proteins were visualized by Western Blotting with rabbit anti-BoNT/A serum (A) or fractions of the scram affinity purified on resin coupled to RAP fusions of mimetic epitopes AIII-1 (B), AIII-L1 (C), or AIII-1 (D-E). Samples were loaded in the following order: (1), pre-stained molecular weight markers; (2) full-length BoNT/A heavy chain; (3) full-length BoNT/A light chain; (4) HisbioRAP-BoNT/AIII-26; (5) HisbioRAP-BoNT/AIII-1; (6) HisbioRAP-BoNT/AIII-L1.

Full-length BoNT heavy and light chains were probed by Western blot with whole anti-BoNT/A antisera (FIG. 6A), or antisera purified against BoNT/AIII-26 (FIG. 6B), BoNT/AIII-1 (FIG. 6C), or BoNT/AIII-L1 (FIG. 6D-E). The AIII-26, AIII-1, and AIII-L1 peptides were loaded as positive controls.

Anti-BoNT/A recognized the BoNT heavy and light chains, but showed no appreciable recognition of the mimetic peptides (FIG. 6A). By contrast, serum purified against the mimetic peptides recognized the BoNT/A light chain, but not the heavy chain (FIG. 6B-E). This confirmed that the mimetic epitopes bind anti-BoNT antibodies that are specific for the light chain. Antibodies purified against BoNT/AIII-1 lost the capacity to recognize the BoNT/A light chain treated with SDS, suggesting that it mimics a structural epitope BoNT/A (FIG. 6D).

Example 8

Immunogenic Properties of BoNT Mimetic Epitopes

Groups of three BALB/c mice were injected with Hisbio-RAP-BoNT/A-mimetic-8, a fusion protein bearing eight mimetic epitopes in series (FIG. 7, bottom panel). Following a four week injection protocol, animals were challenged with 5×LD50 of BoNT/A. The survival rate of control animals was 0% (0/3), while the survival rate of animals receiving the mimetic peptides was 66% (2/3). Multiple trials of the protocol gave consistent results.

Example 9

Receptor Associated Protein-Enhanced Solubility of BoNT Epitopes

Surprisingly and unexpectedly, use of the RAP carrier peptide consistently produced fusion proteins in soluble form, as compared to other constructs which generated largely insoluble proteins that accumulated in inclusion bodies. Three different carriers were tested: BirA, thioredoxin, and RAP. Only RAP fusion proteins were consistently soluble. Although many of the fusions were identical to each other except for the very short BoNT/A-L region and the carrier portion, the difference in the localization and solubility of the proteins was marked.

Example 10

Clostridium perfringens α-Toxin-Induced Secretion of BoNT Epitope Fusion Proteins Fusion proteins including Clostridium perfringens α-toxin as the carrier surprisingly and unexpectedly were secreted from the host cell into the culture media. In media collected from E. coli expressing α-Tox-FBAdel1s, the fusion protein was the only high-molecular weight polypeptide present in significant quantities. Thus, using α-toxin as the carrier facilitates and simplifies purification of the fusion proteins.

Example 11

Detection of Anti-BoNT Antibodies in a Sample

The BoNT real and mimetic epitopes described herein may be used to detect anti-BoNT antibodies in a sample. Samples may be prepared for analysis using methods known in the art based on the specific nature of the sample. For example, the sample may be whole or fractionated blood collected from patients or experimental subjects. Antibodies in the sample may be detected through immunoblotting of sample proteins immobilized on a solid substrate. Anti-BoNT antibodies specifically bound to immobilized proteins may be visualized using an appropriate secondary detection reagent such as a species-specific secondary antibody carrying an enzymatic label. Additionally or alternatively, antibodies present in the sample may be detected using an agglutination test, in which a fluid sample is mixed with BoNT fusion proteins and monitored for the appearance of precipitates. Additionally or alternatively, antibodies present in the sample may be detected using affinity chromatography in which the sample is exposed to BoNT fusion proteins coupled to a polymer resin. Bound antibodies may be eluted from the BoNT-resin and detected using an appropriate secondary detection regent. Additionally or alternatively, antibodies present in the sample may be detected by means of an enzyme linked immunosorbant assay (ELISA) or enzyme immunoassay (EIA). BoNT-fusion proteins may be affixed to a surface and exposed to a fluid sample under conditions conducive to antibody-ligand binding. Specifically bound antibodies may be detected using an appropriate secondary detection reagent. In some embodiments, the methods are provided as kits and contain reagents to detect antibodies according to any of the methods described above.

Example 12

Immunization of a Human or Animal Subject Against BoNT Toxicity

BoNT epitopes described herein may be used to vaccinate humans and animals against BoNT neurotoxicity. BoNT epitopes may be fused to a carrier protein and administered to human and animal subjects in the presence of adjuvants such as but not limited to aluminum salts and liposomes. Those skilled, in the art will understand that any number of pharmaceutically acceptable adjuvants can also be used. Carrier proteins having adjuvant properties themselves, such as cholera toxin B, may also be used. To maximize the spectrum of protection, vaccination compositions may include several real or mimetic BoNT epitopes. Real epitopes may be derived, from a single BoNT serotype or several BoNT serotypes. Immunogenic compositions may be administered to a human or animal subjects intramuscularly, subdermally, intranasally, or through any other suitable route. Immunogenic compositions may also take the form of nucleic acid vaccines, in which nucleic acids encoding BoNT epitopes are administered to human or animal subjects. Alternatively, sequences encoding BoNT epitopes may be incorporated into host organisms such as Salmonella for oral or intranasal administration. Administration can be provided as an initial dose, followed by one or more booster doses. Booster doses can be provided a day, two days, three days, a week, two weeks, three weeks, one, two, three, six or twelve months after an initial dose. A booster dose may be administered after an evaluation of the subject's antibody titer.

TABLE 1

Oligonucleotide pairs encoding BoNT light chain epitopes

| Designation | Sequence (SEQ ID NOS 1-10, respectively, in order of apperance) | Fusion |
|---|---|---|
| Del1-5' | 5'-gtacctggatccgttccggttagctattatgatagcacgtatttaagcacctaagcctgca | HisbioRAP- |
| Del1-3' | 5'-ggcttagtgcttaaatacgtgctatcataatagctaaccggaacggatccag | del1s |
| Del4-5' | 5'-gtacctggatcctttaatggtcaaaataccgaaattaataatatgaattttaccaaataagcctgca | HisbioRAP- |
| Del4-3' | 5'-ggcttatttggtaaaattcatattattaattcggtattttgaccattaaaggatccag | del4s |
| A-Zn5' | 5'-ctggatcccatgaactgattcatgcgggccatcgcctgtatggcattgtcgactaaagcctgca | FlisbioRAP- |
| A-Zn3' | 5'-ggctttagtcgacaatgccatacaggcgatggcccgcatgaatcagttcatgggatccaggtac | A-Zn |
| Fdel1-5' | 5'-ctggatccggcagcagcgcgtattatgatccgaactatctgaccaccgtcgactaagcctgca | HisbioRAP- |
| Fdel1-3' | 5'-ggcttagtcgacggtggtcagatagttcggatcataatacgcgctgctgccggatccaggtac | Fdel1s |
| Bdel1-5' | 5'-ctggatccgatgtgtgcgaatattatgatccggattatctgaacaccgtcgactaagcctgca | HisbioRAP- |
| Bdel1-3' | 5'-ggcttagtcgacggtgttcagataatccggatcataatattcgcacacatcggatccaggtac | Bdel1s |

TABLE 2

Murine BoNT/FBA-del1-induced immune response.
Results are presented as fold increase in $OD_{450}$
over pre-immune sera in a direct ELISA.

| | Animal | | | |
|---|---|---|---|---|
| | A | | B | |
| | Antigen | | | |
| | α-Tox-FBAdel1s | HisbioRAP-FBAdel1s | α-Tox-FBAdel1s | HisbioRAP-FBAdel1s |
| Bleed 1 | 3.9X | 9.5X | 1.3X | 4.9X |
| Bleed 2 | 2.8X | 18.8X | 1.3X | 9.0X |
| Bleed 3 | 15X | 33.7X | 4.1X | 30X |

TABLE 3

BoNT/A mimetic epitopes

| Designation | Sequence | SEQ ID NO: |
|---|---|---|
| *Sequences isolated from peptide display utilizing protein III* | | |
| BoNT/AIII-0 | IKSNPQTSNEFL | 11 |
| BoNT/AIII-1 | TAPTMPITTPRL | 12 |
| BoNTLAIII-L1 | EQPMQHLSGAFA | 13 |
| BoNT/AIII-3 | TYLQIIPDVGYI | 14 |
| BoNT/AIII-6 | AIGDINPPHLDT | 15 |
| BoNT/AIII-9 | VQSSMLPIPSTP | 16 |
| BoNT/AIII-24 | VQRSTFILPTTP | 17 |
| BoNT/AIII-26 | DGDINPPTRTML | 18 |
| BoNT/AIII-27 | IKSNPQTSNEFL | 19 |
| *Sequences isolated from peptide display utilizing protein VII* | | |
| BoNT/AVII1-3 | DPTRFHSRPPAI | 19 |
| BoNT/AVII1-6 | DFGDHNPPEQSS | 20 |
| BoNT/AVII1-12 | PLHPSQMPLSLI | 21 |
| BoNT/AVII1-13 | APTSPVTHGPQL | 22 |
| BoNT/AVII1-16 | QEALGLIVESHT | 23 |
| BoNT/AVII1-19 | SLTSPITPRPEY | 24 |
| BoNT/AVII1-20 | DVGDLGRPVHFI | 25 |
| BoNT/AVII3-6 | WCASVQRPLTLV | 26 |
| BoNT/AVII3-7 | FGPRSLPDHYYD | 27 |
| BoNT/AVII3-13 | PTFGRQIPLSVI | 28 |
| BoNT/AVII3-17 | VGADVGTLSAAF | 29 |
| BoNT/AVII5-4 | YSYWDSTFLDTL | 30 |
| BoNT/AVII5-18 | QAPLSLVQPFRD | 31 |

TABLE 4

BoNT/B mimetic epitopes.
Sequences isolated by peptide display using protein VII.

| Designation | Sequence | SEQ ID NO: |
|---|---|---|
| BoNT/BVII-1 | GLARRYVLWPVAS | 32 |
| BoNT/BVII-2 | NDQRRVWQAQRC | 33 |
| BoNT/BVII-3 | GLAQRWATAHCW | 34 |
| BoNT/BVII-4 | HARHLWHIASTA | 35 |
| BoNT/BVII-5 | FHHHRYLTCAAA | 36 |
| BoNT/BVII-6 | DGPRHLLRHHAI | 37 |
| BoNT/BVII-7 | GLARRYVLWPVA | 38 |
| BoNT/BVII-8 | DQPRRLYHVTAP | 39 |
| BoNT/BVII-9 | LGHAWSRWHVPI | 40 |
| BoNT/BVII-10 | DVTRRHWSPSPS | 41 |
| BoNT/BVII-11 | RLPHLHPWHYAV | 42 |
| BoNT/BVII-12 | WWRVTHTAQSVS | 43 |
| BoNT/BVII-13 | RWSLHSHHAPKV | 44 |
| BoNT/BVII-14 | AGMWGWRHAHTI | 45 |
| BoNT/BVII-15 | PLHAYFHALKAG | 46 |
| BoNT/BVII-16 | HWRHYNHSQAPV | 47 |
| BoNT/BVII-17 | SRHVFVRHNQHC | 48 |

TABLE 5

BoNT/E mimetic epitopes.
Sequences isolated by peptide display using protein VII.

| Designation | Sequence | SEQ ID NO: |
|---|---|---|
| BoNT/EVII-1 | KRVAPPEFGIPI | 49 |
| BoNT/EVII-2 | LRGLPRCCTYAW | 50 |
| BoNT/EVII-3 | HRLPFSFHHSHV | 51 |

TABLE 5-continued

BoNT/E mimetic epitopes. Sequences isolated by peptide display using protein VII.

| Designation | Sequence | SEQ ID NO: |
|---|---|---|
| BoNT/EVII-4 | WSPLARLCARSC | 52 |
| BoNT/EVII-5 | WRAGHLAWLHGM | 53 |
| BoNT/EVII-6 | AHRRAFHGAHHV | 54 |
| BoNT/EVII-7 | HHPFPTPVLLLC | 55 |
| BoNT/EVII-8 | HVHRPFGHTHPP | 56 |
| BoNT/EVII-9 | HHHFLHRSPSTV | 57 |
| BoNT/EVII-10 | PDRYSGPFTNVY | 58 |
| BoNT/EVII-11 | YRVAPPPGLMAN | 59 |
| BoNT/EVII-12 | TLARRHMLINTF | 60 |
| BoNT/EVII-13 | LRHWHCPTKLQT | 61 |

TABLE 6

RAP-binding peptides isolated by phage display.

| Designation | Sequence | SEQ ID NO: |
|---|---|---|
| RAP-bp1 | APAWRAPAQQLG | 62 |
| RAP-bp2 | HLALHAHLHHLL | 63 |
| RAP-bp3 | PHLWFHGFLELC | 64 |
| RAP-bp4 | PLRLAPLLCYVK | 65 |

TABLE 7

Nickel-binding peptides identified by phage display.

| Designation | Sequence | SEQ ID NO: |
|---|---|---|
| Ni-bp1 | HPGRPHHAHRHH | 66 |
| Ni-bp2 | HTHHPVHRATPE | 67 |
| Ni-bpi | PHSHEHHSARLD | 68 |
| Ni-bp4 | HRHLVKHRELSP | 69 |
| Ni-bp5 | RDHRVTASHHRH | 70 |
| Ni-bp6 | DLPRRAHHSRPC | 71 |
| Ni-bp7 | ARRHHHTPPALH | 72 |
| Ni-bp8 | PGPRRVHHHTTS | 73 |
| Ni-bp9 | STGHSRYHGHHR | 74 |
| Ni-bp10 | ADFRRAHAHPPR | 75 |
| Ni-bp11 | PRRHHDHSPPRI | 76 |
| Ni-bp12 | DTSRRHHRPPVH | 77 |
| Ni-bp13 | PHQCLPPHHARF | 78 |
| Ni-bp14 | IPPHHHHSTNTR | 79 |
| Ni-bp15 | HRPHGSLGHPKL | 80 |
| Ni-bp16 | TLPHHAQRAPYH | 81 |
| Ni-bp17 | PPSKTAPHHRVH | 82 |
| Ni-bp18 | PLHHHPTRAPLT | 83 |
| Ni-bp19 | AHHAHPPRPALS | 84 |
| Ni-bp20 | GAHHIPKHDHVA | 85 |
| Ni-bp21 | TTAHPIHAPCSR | 86 |
| Ni-bp22 | PLHHHPTRAPLT | 87 |

TABLE 8

Streptavidin-binding peptides isolated by phage display.

| Designation | Sequence | SEQ ID NO: |
|---|---|---|
| SA-bp1 | VIWSHPQNYTIGS | 88 |
| SA-bp2 | SFDRFLATGAMY | 89 |
| SA-bp3 | PGPDCATYPFCN | 90 |
| SA-bp4 | WHPQSGLTPCTI | 91 |

---

SEQUENCE LISTING

<160> NUMBER OF SEQ ID NOS: 137

<210> SEQ ID NO 1
<211> LENGTH: 61
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1
gtacctggat ccgttccggt tagctattat gatagcacgt atttaagcac ctaagcctgc    60

```
a                                                              61

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcttaggtg cttaaatacg tgctatcata atagctaacc ggaacggatc cag        53

<210> SEQ ID NO 3
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtacctggat cctttaatgg tcaaaatacc gaaattaata atatgaattt taccaaataa  60
gcctgca                                                            67

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcttatttg gtaaaattca tattattaat ttcggtattt tgaccattaa aggatccag   59

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctggatccca tgaactgatt catgcgggcc atcgcctgta tggcattgtc gactaaagcc  60
tgca                                                               64

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggctttagtc gacaatgcca tacaggcgat ggcccgcatg aatcagttca tgggatccag  60
gtac                                                               64

<210> SEQ ID NO 7
<211> LENGTH: 63
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 7
ctggatccgg cagcagcgcg tattatgatc cgaactatct gaccaccgtc gactaagcct    60
gca                                                                  63

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggcttagtcg acggtggtca gatagttcgg atcataatac gcgctgctgc cggatccagg    60
tac                                                                  63

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctggatccga tgtgtgcgaa tattatgatc cggattatct gaacaccgtc gactaagcct    60
gca                                                                  63

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggcttagtcg acggtgttca gataatccgg atcataatat tcgcacacat cggatccagg    60
tac                                                                  63

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Lys Ser Asn Pro Gln Thr Ser Asn Glu Phe Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Thr Ala Pro Thr Met Pro Ile Thr Thr Pro Arg Leu
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Glu Gln Pro Met Gln His Leu Ser Gly Ala Phe Ala
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Thr Tyr Leu Gln Thr Ile Pro Asp Val Gly Tyr Ile
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Ala Ile Gly Asp Ile Asn Pro Pro His Leu Asp Thr
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Val Gln Ser Ser Met Leu Pro Ile Pro Ser Thr Pro
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Val Gln Arg Ser Thr Phe Ile Leu Pro Thr Thr Pro
1               5                   10
```

<210> SEQ ID NO 18
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 18

Asp Gly Asp Ile Asn Pro Pro Thr Arg Thr Met Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Pro Thr Arg Phe His Ser Arg Pro Pro Ala Ile
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Phe Gly Asp His Asn Pro Pro Glu Gln Ser Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Leu His Pro Ser Gln Met Pro Leu Ser Leu Ile
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Pro Thr Ser Pro Val Thr His Gly Pro Gln Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Glu Ala Leu Gly Leu Ile Val Glu Ser His Thr
1               5                   10
```

```
<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Leu Thr Ser Pro Ile Thr Pro Arg Pro Glu Tyr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Val Gly Asp Leu Gly Arg Pro Val His Phe Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Cys Ala Ser Val Gln Arg Pro Leu Thr Leu Val
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Gly Pro Arg Ser Leu Pro Asp His Tyr Tyr Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Thr Phe Gly Arg Gln Ile Pro Leu Ser Val Ile
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

```
Val Gly Ala Asp Val Gly Thr Leu Ser Ala Ala Phe
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Tyr Ser Tyr Trp Asp Ser Thr Phe Leu Asp Thr Leu
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Gln Ala Pro Leu Ser Leu Val Gln Pro Phe Arg Asp
1               5                   10
```

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Gly Leu Ala Arg Arg Tyr Val Leu Trp Pro Val Ala Ser
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Asn Asp Gln Arg Arg Val Trp Gln Ala Gln Arg Cys
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Gly Leu Ala Gln Arg Trp Ala Thr Ala His Cys Trp
1               5                   10
```

<210> SEQ ID NO 35
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 35

His Ala Arg His Leu Trp His Ile Ala Ser Thr Ala
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe His His His Arg Tyr Leu Thr Cys Ala Ala Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Gly Pro Arg His Leu Leu Arg His His Ala Ile
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Leu Ala Arg Arg Tyr Val Leu Trp Pro Val Ala
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Gln Pro Arg Arg Leu Tyr His Val Thr Ala Pro
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Gly His Ala Trp Ser Arg Trp His Val Pro Ile
1               5                   10
```

```
<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Val Thr Arg Arg His Trp Ser Pro Ser Pro Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Leu Pro His Leu His Pro Trp His Tyr Ala Val
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Trp Arg Val Thr His Thr Ala Gln Ser Val Ser
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Trp Ser Leu His Ser His His Ala Pro Lys Val
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Gly Met Trp Gly Trp Arg His Ala His Thr Ile
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 46

Pro Leu His Ala Tyr Phe His Ala Leu Lys Ala Gly
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Trp Arg His Tyr Asn His Ser Gln Ala Pro Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Arg His Val Phe Val Arg His Asn Gln His Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Arg Val Ala Pro Pro Glu Phe Gly Ile Pro Ile
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Arg Gly Leu Pro Arg Cys Cys Thr Tyr Ala Trp
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Arg Leu Pro Phe Ser His Ser His Ser His Val
1               5                   10

<210> SEQ ID NO 52
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 52

Trp Ser Pro Leu Ala Arg Leu Cys Ala Arg Ser Cys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Arg Ala Gly His Leu Ala Trp Leu His Gly Met
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala His Arg Arg Ala Phe His Gly Ala His His Val
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

His His Pro Phe Pro Thr Pro Val Leu Leu Leu Cys
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Val His Arg Pro Phe Gly His Thr His Pro Pro
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His His His Phe Leu His Arg Ser Pro Ser Thr Val
1               5                   10
```

```
<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Asp Arg Tyr Ser Gly Pro Phe Thr Asn Val Tyr
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Tyr Arg Val Ala Pro Pro Gly Leu Met Ala Asn
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Leu Ala Arg Arg His Met Leu Ile Asn Thr Phe
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Arg His Trp His Cys Pro Thr Lys Leu Gln Thr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Pro Ala Trp Arg Ala Pro Ala Gln Gln Leu Gly
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

His Leu Ala Leu His Ala His Leu His His Leu Leu
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro His Leu Trp Phe His Gly Phe Leu Glu Leu Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Leu Arg Leu Ala Pro Leu Leu Cys Tyr Val Lys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Pro Gly Arg Pro His His Ala His Arg His His
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Thr His His Pro Val His Arg Ala Thr Pro Glu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro His Ser His Glu His His Ser Ala Arg Leu Asp
1               5                   10

<210> SEQ ID NO 69
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

His Arg His Leu Val Lys His Arg Glu Leu Ser Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Asp His Arg Val Thr Ala Ser His His Arg His
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Leu Pro Arg Arg Ala His His Ser Arg Pro Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Arg Arg His His His Thr Pro Pro Ala Leu His
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Gly Pro Arg Arg Val His His His Thr Thr Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Thr Gly His Ser Arg Tyr His Gly His His Arg
```

```
<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Asp Phe Arg Arg Ala His Ala His Pro Pro Arg
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Pro Arg Arg His His Asp His Ser Pro Pro Arg Ile
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Thr Ser Arg Arg His His Arg Pro Pro Val His
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro His Gln Cys Leu Pro Pro His His Ala Arg Phe
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Pro Pro His His His His Ser Thr Asn Thr Arg
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 80

His Arg Pro His Gly Ser Leu Gly His Pro Lys Leu
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Leu Pro His His Ala Gln Arg Ala Pro Tyr His
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Pro Ser Lys Thr Ala Pro His His Arg Val His
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Pro Leu His His His Pro Thr Arg Ala Pro Leu Thr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala His His Ala His Pro Pro Arg Pro Ala Leu Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ala His His Ile Pro Lys His Asp His Val Ala
1               5                   10

<210> SEQ ID NO 86

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Thr Ala His Pro Ile His Ala Pro Cys Ser Arg
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Leu His His His Pro Thr Arg Ala Pro Leu Thr
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Val Ile Trp Ser His Pro Gln Asn Tyr Thr Ile Gly Ser
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Phe Asp Arg Phe Leu Ala Thr Gly Ala Met Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Gly Pro Asp Cys Ala Thr Tyr Pro Phe Cys Asn
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Trp His Pro Gln Ser Gly Leu Thr Pro Cys Thr Ile
1               5                   10

<210> SEQ ID NO 92
<211> LENGTH: 448
<212> TYPE: PRT
<213> ORGANISM: Clostridium botulinum

<400> SEQUENCE: 92

Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

```
Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

<210> SEQ ID NO 93
<211> LENGTH: 13
<212> TYPE: PRT
<213> ORGANISM: Clostridium botulinum

<400> SEQUENCE: 93

Val Pro Val Ser Tyr Tyr Asp Ser Thr Tyr Leu Ser Thr
1               5                   10

<210> SEQ ID NO 94
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Phe Thr Asn Pro Glu Glu Gly Asp Leu Asn Pro Pro Pro Glu Ala Lys
1               5                   10                  15

Gln Val Pro Val Ser Tyr Tyr Asp Ser Thr Tyr Leu Ser Thr
            20                  25                  30

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Pro Val Ser Tyr Tyr Asp Ser Thr Tyr Leu Ser Thr Asp Asn Glu
1               5                   10                  15

Lys Asp Asn Tyr Leu Lys Gly
            20

<210> SEQ ID NO 96
<211> LENGTH: 19
<212> TYPE: PRT
<213> ORGANISM: Clostridium botulinum

<400> SEQUENCE: 96

Asp Phe Thr Phe Gly Phe Glu Glu Ser Leu Glu Val Asp Thr Asn Pro
1               5                   10                  15

Leu Leu Gly

<210> SEQ ID NO 97
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 97

Ser Pro Asp Phe Thr Phe Gly Phe Glu Glu Ser Leu Glu Val Asp Thr
1               5                   10                  15

Asn Pro Leu Leu Gly Ala Gly Lys Phe Ala Thr Asp Pro
            20                  25

<210> SEQ ID NO 98
<211> LENGTH: 58
<212> TYPE: PRT
<213> ORGANISM: Clostridium botulinum

<400> SEQUENCE: 98

Lys Met Leu Thr Glu Ile Tyr Thr Glu Asp Asn Phe Val Lys Phe Phe
1               5                   10                  15

Lys Val Leu Asn Arg Lys Thr Tyr Leu Asn Phe Asp Lys Ala Val Phe
                20                  25                  30

Lys Ile Asn Ile Val Pro Lys Val Asn Tyr Thr Ile Tyr Asp Gly Phe
            35                  40                  45

Asn Leu Arg Asn Thr Asn Leu Ala Ala Asn
        50                  55

<210> SEQ ID NO 99
<211> LENGTH: 23
<212> TYPE: PRT
<213> ORGANISM: Clostridium botulinum

<400> SEQUENCE: 99

Phe Asn Gly Gln Asn Thr Glu Ile Asn Asn Met Asn Phe Thr Lys Leu
1               5                   10                  15

Lys Asn Phe Thr Gly Leu Phe
            20

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Phe Asn Gly Gln Asn Thr Glu Ile Asn Asn Met Asn Phe Thr Lys
1               5                   10                  15

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Phe Asn Gly Gln Asn Thr Glu Ile Asn Asn Met Asn Phe Thr Lys Leu
1               5                   10                  15

Lys Asn Phe Thr Gly Leu Phe Glu Phe Tyr Lys
            20                  25

<210> SEQ ID NO 102
```

<211> LENGTH: 19
<212> TYPE: PRT
<213> ORGANISM: Clostridium botulinum

<400> SEQUENCE: 102

Ala Lys Gln Val Pro Val Ser Tyr Tyr Asp Ser Thr Tyr Leu Ser Thr
1               5                   10                  15
Asp Asn Glu

<210> SEQ ID NO 103
<211> LENGTH: 19
<212> TYPE: PRT
<213> ORGANISM: Clostridium botulinum

<400> SEQUENCE: 103

Val Thr Ser Pro Lys Ser Gly Tyr Tyr Asp Pro Asn Tyr Leu Ser Thr
1               5                   10                  15
Asp Ser Asp

<210> SEQ ID NO 104
<211> LENGTH: 19
<212> TYPE: PRT
<213> ORGANISM: Clostridium botulinum

<400> SEQUENCE: 104

Pro Thr Ser Lys Tyr Gln Ser Tyr Tyr Asp Pro Ser Tyr Leu Ser Thr
1               5                   10                  15
Asp Glu Gln

<210> SEQ ID NO 105
<211> LENGTH: 19
<212> TYPE: PRT
<213> ORGANISM: Clostridium botulinum

<400> SEQUENCE: 105

Phe Asn Arg Asp Val Cys Glu Tyr Tyr Asp Pro Asp Tyr Leu Asn Thr
1               5                   10                  15
Asn Asp Lys

<210> SEQ ID NO 106
<211> LENGTH: 19
<212> TYPE: PRT
<213> ORGANISM: Clostridium botulinum

<400> SEQUENCE: 106

Phe Ser Lys Asp Val Tyr Glu Tyr Tyr Asp Pro Thr Tyr Leu Lys Thr
1               5                   10                  15
Asp Ala Glu

<210> SEQ ID NO 107
<211> LENGTH: 19
<212> TYPE: PRT
<213> ORGANISM: Clostridium botulinum

<400> SEQUENCE: 107

Leu Ile Glu Gly Ala Ser Glu Tyr Tyr Asp Pro Asn Tyr Leu Arg Thr
1               5                   10                  15
Asp Ser Asp

<210> SEQ ID NO 108
<211> LENGTH: 19

```
<212> TYPE: PRT
<213> ORGANISM: Clostridium botulinum

<400> SEQUENCE: 108

Leu Lys Asn Gly Asp Ser Ser Tyr Tyr Asp Pro Asn Tyr Leu Gln Ser
1               5                   10                  15

Asp Glu Glu

<210> SEQ ID NO 109
<211> LENGTH: 19
<212> TYPE: PRT
<213> ORGANISM: Clostridium botulinum

<400> SEQUENCE: 109

Leu Glu Asn Gly Ser Ser Ala Tyr Tyr Asp Pro Asn Tyr Leu Thr Thr
1               5                   10                  15

Asp Ala Glu

<210> SEQ ID NO 110
<211> LENGTH: 39
<212> TYPE: PRT
<213> ORGANISM: Clostridium botulinum

<400> SEQUENCE: 110

Ile Arg Phe Ser Pro Asp Phe Thr Phe Gly Phe Glu Glu Ser Leu Glu
1               5                   10                  15

Val Asp Thr Asn Pro Leu Leu Gly Ala Gly His Glu Leu Ile His Ala
                20                  25                  30

Gly His Arg Leu Tyr Gly Ile
            35

<210> SEQ ID NO 111
<211> LENGTH: 39
<212> TYPE: PRT
<213> ORGANISM: Clostridium botulinum

<400> SEQUENCE: 111

Ile Ser Ile Ser Pro Arg Phe Met Leu Thr Tyr Ser Asn Ala Thr Asn
1               5                   10                  15

Asp Val Gly Glu Gly Arg Phe Ser Lys Ser His Glu Leu Asn His Ala
                20                  25                  30

Met His Asn Leu Tyr Gly Ile
            35

<210> SEQ ID NO 112
<211> LENGTH: 39
<212> TYPE: PRT
<213> ORGANISM: Clostridium botulinum

<400> SEQUENCE: 112

Leu Lys Val Ala Pro Glu Phe Leu Leu Thr Phe Ser Asp Val Thr Ser
1               5                   10                  15

Asn Gln Ser Ser Ala Val Leu Gly Lys Ser His Glu Leu Thr His Ser
                20                  25                  30

Leu His Gln Leu Tyr Gly Ile
            35

<210> SEQ ID NO 113
<211> LENGTH: 39
<212> TYPE: PRT
<213> ORGANISM: Clostridium botulinum
```

<400> SEQUENCE: 113

Met Lys Phe Cys Pro Glu Tyr Val Ser Val Phe Asn Asn Val Gln Glu
1               5                   10                  15

Asn Lys Gly Ala Ser Ile Phe Asn Arg Arg His Glu Leu Ile His Val
            20                  25                  30

Leu His Gly Leu Tyr Gly Ile
            35

<210> SEQ ID NO 114
<211> LENGTH: 39
<212> TYPE: PRT
<213> ORGANISM: Clostridium botulinum

<400> SEQUENCE: 114

Ile Arg Phe Cys Pro Ser Cys Leu Asn Val Phe Asn Asn Val Gln Glu
1               5                   10                  15

Asn Lys Asp Thr Ser Ile Phe Ser Arg Arg His Glu Leu Ile His Val
            20                  25                  30

Leu His Gly Leu Tyr Gly Ile
            35

<210> SEQ ID NO 115
<211> LENGTH: 39
<212> TYPE: PRT
<213> ORGANISM: Clostridium botulinum

<400> SEQUENCE: 115

Met Ala Phe Cys Pro Glu Tyr Val Pro Thr Phe Asp Asn Val Ile Glu
1               5                   10                  15

Asn Ile Thr Ser Leu Thr Ile Gly Lys Ser His Glu Leu Ile His Val
            20                  25                  30

Leu His Gly Leu Tyr Gly Met
            35

<210> SEQ ID NO 116
<211> LENGTH: 30
<212> TYPE: PRT
<213> ORGANISM: Clostridium botulinum

<400> SEQUENCE: 116

Val Thr Phe Ser Pro Glu Tyr Ser Phe Arg Phe Asn Asp Asn Ser Met
1               5                   10                  15

Asn His Glu Leu Ile His Ser Leu His Gly Leu Tyr Gly Ala
            20                  25                  30

<210> SEQ ID NO 117
<211> LENGTH: 36
<212> TYPE: PRT
<213> ORGANISM: Clostridium botulinum

<400> SEQUENCE: 117

Val Thr Phe Ser Pro Glu Tyr Glu Tyr Thr Phe Asn Asp Ile Ser Gly
1               5                   10                  15

Gly Tyr Asn Ser Ser Thr Glu His Glu Leu Ile His Ala Leu His Gly
            20                  25                  30

Leu Tyr Gly Ala
            35

<210> SEQ ID NO 118

<211> LENGTH: 49
<212> TYPE: PRT
<213> ORGANISM: Clostridium botulinum

<400> SEQUENCE: 118

Val Asp Lys Leu Lys Phe Asp Lys Leu Tyr Lys Met Leu Thr Glu Ile
1               5                   10                  15

Tyr Thr Glu Asp Asn Phe Val Lys Phe Phe Lys Val Leu Asn Arg Lys
            20                  25                  30

Thr Tyr Leu Asn Phe Asp Lys Ala Val Phe Lys Ile Asn Ile Val Pro
        35                  40                  45

Lys

<210> SEQ ID NO 119
<211> LENGTH: 49
<212> TYPE: PRT
<213> ORGANISM: Clostridium botulinum

<400> SEQUENCE: 119

Val Asn Arg Asn Lys Phe Val Glu Leu Tyr Asn Glu Leu Thr Gln Ile
1               5                   10                  15

Phe Thr Glu Phe Asn Tyr Ala Lys Ile Tyr Asn Val Gln Asn Arg Lys
            20                  25                  30

Ile Tyr Leu Ser Asn Val Tyr Thr Pro Val Thr Ala Asn Ile Leu Asp
        35                  40                  45

Asp

<210> SEQ ID NO 120
<211> LENGTH: 49
<212> TYPE: PRT
<213> ORGANISM: Clostridium botulinum

<400> SEQUENCE: 120

Val Asn Ile Asp Lys Phe Asn Ser Leu Tyr Ser Asp Leu Thr Asn Val
1               5                   10                  15

Met Ser Glu Val Val Tyr Ser Ser Gln Tyr Asn Val Lys Asn Arg Thr
            20                  25                  30

His Tyr Phe Ser Arg His Tyr Leu Pro Val Phe Ala Asn Ile Leu Asp
        35                  40                  45

Asp

<210> SEQ ID NO 121
<211> LENGTH: 50
<212> TYPE: PRT
<213> ORGANISM: Clostridium botulinum

<400> SEQUENCE: 121

Ile Asp Val Glu Ser Phe Asp Lys Leu Tyr Lys Ser Leu Met Phe Gly
1               5                   10                  15

Phe Thr Glu Thr Asn Ile Ala Glu Asn Tyr Lys Ile Lys Thr Arg Ala
            20                  25                  30

Ser Tyr Phe Ser Asp Ser Leu Pro Pro Val Lys Ile Lys Asn Leu Leu
        35                  40                  45

Asp Asn
    50

<210> SEQ ID NO 122
<211> LENGTH: 50
<212> TYPE: PRT

<213> ORGANISM: Clostridium botulinum

<400> SEQUENCE: 122

Val Asp Lys Asp Lys Phe Asp Lys Leu Tyr Lys Ala Leu Met Phe Gly
1               5                   10                  15

Phe Thr Glu Thr Asn Leu Ala Gly Glu Tyr Gly Ile Lys Thr Arg Tyr
            20                  25                  30

Ser Tyr Phe Ser Glu Tyr Leu Pro Pro Ile Lys Thr Glu Lys Leu Leu
        35                  40                  45

Asp Asn
    50

<210> SEQ ID NO 123
<211> LENGTH: 50
<212> TYPE: PRT
<213> ORGANISM: Clostridium botulinum

<400> SEQUENCE: 123

Val Asn Glu Asp Lys Phe Gln Ile Leu Tyr Asn Ser Ile Met Tyr Gly
1               5                   10                  15

Phe Thr Glu Ile Glu Leu Gly Lys Lys Phe Asn Ile Lys Thr Arg Leu
            20                  25                  30

Ser Tyr Phe Ser Met Asn His Asp Pro Val Lys Ile Pro Asn Leu Leu
        35                  40                  45

Asp Asp
    50

<210> SEQ ID NO 124
<211> LENGTH: 48
<212> TYPE: PRT
<213> ORGANISM: Clostridium botulinum

<400> SEQUENCE: 124

Val Asn Ile Asn Lys Phe Asn Asp Ile Phe Lys Lys Leu Tyr Ser Phe
1               5                   10                  15

Thr Glu Phe Asp Leu Ala Thr Lys Phe Gln Val Lys Cys Arg Gln Thr
            20                  25                  30

Tyr Ile Gly Gln Tyr Lys Tyr Phe Lys Leu Ser Asn Leu Asn Asp
        35                  40                  45

<210> SEQ ID NO 125
<211> LENGTH: 48
<212> TYPE: PRT
<213> ORGANISM: Clostridium botulinum

<400> SEQUENCE: 125

Val Asn Glu Asn Lys Phe Asn Glu Ile Tyr Lys Lys Leu Tyr Ser Phe
1               5                   10                  15

Thr Glu Ile Asp Leu Ala Asn Lys Phe Lys Val Lys Cys Arg Asn Thr
            20                  25                  30

Tyr Phe Ile Lys Tyr Gly Phe Leu Lys Val Pro Asn Leu Asp Asp
        35                  40                  45

<210> SEQ ID NO 126
<211> LENGTH: 50
<212> TYPE: PRT
<213> ORGANISM: Clostridium botulinum

<400> SEQUENCE: 126

Val Asn Tyr Thr Ile Tyr Asp Gly Phe Asn Leu Arg Asn Thr Asn Leu

```
1               5                   10                  15
Ala Ala Asn Phe Asn Gly Gln Asn Thr Glu Ile Asn Asn Met Asn Phe
            20                  25                  30
Thr Lys Leu Lys Asn Phe Thr Gly Leu Phe Glu Phe Tyr Lys Leu Leu
            35                  40                  45
Cys Val
    50
```

<210> SEQ ID NO 127
<211> LENGTH: 48
<212> TYPE: PRT
<213> ORGANISM: Clostridium botulinum

<400> SEQUENCE: 127

```
Asn Val Tyr Asp Ile Gln Asn Gly Phe Asn Ile Pro Lys Ser Asn Leu
1               5                   10                  15
Asn Val Leu Phe Met Gly Gln Asn Leu Ser Arg Asn Pro Ala Leu Arg
            20                  25                  30
Lys Val Asn Pro Glu Asn Met Leu Tyr Leu Phe Thr Lys Phe Cys His
            35                  40                  45
```

<210> SEQ ID NO 128
<211> LENGTH: 48
<212> TYPE: PRT
<213> ORGANISM: Clostridium botulinum

<400> SEQUENCE: 128

```
Asn Ile Tyr Thr Ile Arg Asp Gly Phe Asn Leu Thr Asn Lys Gly Phe
1               5                   10                  15
Asn Ile Glu Asn Ser Gly Gln Asn Ile Glu Arg Asn Pro Ala Leu Gln
            20                  25                  30
Lys Leu Ser Ser Glu Ser Val Val Asp Leu Phe Thr Lys Val Cys Leu
            35                  40                  45
```

<210> SEQ ID NO 129
<211> LENGTH: 49
<212> TYPE: PRT
<213> ORGANISM: Clostridium botulinum

<400> SEQUENCE: 129

```
Glu Ile Tyr Thr Ile Glu Glu Gly Phe Asn Ile Ser Asp Lys Asp Met
1               5                   10                  15
Glu Lys Glu Tyr Arg Gly Gln Asn Lys Ala Ile Asn Lys Gln Ala Tyr
            20                  25                  30
Glu Glu Ile Ser Lys Glu His Leu Ala Val Tyr Lys Ile Gln Met Cys
            35                  40                  45
Lys
```

<210> SEQ ID NO 130
<211> LENGTH: 49
<212> TYPE: PRT
<213> ORGANISM: Clostridium botulinum

<400> SEQUENCE: 130

```
Thr Ile Tyr Thr Gln Asn Glu Gly Phe Asn Ile Ala Ser Lys Asn Leu
1               5                   10                  15
Lys Thr Glu Phe Asn Gly Gln Asn Lys Ala Val Asn Lys Glu Ala Tyr
            20                  25                  30
Glu Glu Ile Ser Leu Glu His Leu Val Ile Tyr Arg Ile Ala Met Cys
```

```
                35                  40                  45
Lys

<210> SEQ ID NO 131
<211> LENGTH: 49
<212> TYPE: PRT
<213> ORGANISM: Clostridium botulinum

<400> SEQUENCE: 131

Thr Ile Tyr Asn Asp Thr Glu Gly Phe Asn Ile Glu Ser Lys Asp Leu
1               5                   10                  15

Lys Ser Glu Tyr Lys Gly Gln Asn Met Arg Val Asn Thr Asn Ala Phe
            20                  25                  30

Arg Asn Val Asp Gly Ser Gly Leu Val Ser Lys Leu Ile Gly Leu Cys
        35                  40                  45

Lys

<210> SEQ ID NO 132
<211> LENGTH: 47
<212> TYPE: PRT
<213> ORGANISM: Clostridium botulinum

<400> SEQUENCE: 132

Ser Ile Tyr Asn Ile Ser Glu Gly Tyr Asn Ile Asn Asn Leu Lys Val
1               5                   10                  15

Asn Phe Arg Gly Gln Asn Ala Asn Leu Asn Pro Arg Ile Ile Thr Pro
            20                  25                  30

Ile Thr Gly Arg Gly Leu Val Lys Lys Ile Ile Arg Phe Cys Lys
        35                  40                  45

<210> SEQ ID NO 133
<211> LENGTH: 47
<212> TYPE: PRT
<213> ORGANISM: Clostridium botulinum

<400> SEQUENCE: 133

Asp Ile Tyr Thr Val Ser Glu Gly Phe Asn Ile Gly Asn Leu Ala Val
1               5                   10                  15

Asn Asn Arg Gly Gln Asn Ile Lys Leu Asn Pro Lys Ile Ile Asp Ser
            20                  25                  30

Ile Pro Asp Lys Gly Leu Val Glu Lys Ile Val Lys Phe Cys Lys
        35                  40                  45

<210> SEQ ID NO 134
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Gly Ser Ser His His His His His His Ser Ser Gly Leu Val Pro
1               5                   10                  15

Arg Gly Ser His Met Leu Asp Met Ala Ser Ser Leu Arg Gln Ile Leu
            20                  25                  30

Asp Ser Gln Lys Met Glu Trp Arg Ser Asn Ala Gly Gly Ser Gly Arg
        35                  40                  45

Asp Asn Arg Val Ile Ser Arg Glu Lys Asn Gln Pro Lys Pro Ser Pro
    50                  55                  60
```

-continued

Lys Arg Glu Ser Gly Glu Phe Arg Met Glu Lys Leu Asn Gln Leu
65                  70                  75                  80

Trp Glu Lys Ala Gln Arg Leu His Leu Pro Pro Val Arg Leu Ala Glu
            85                  90                  95

Leu His Ala Asp Leu Lys Ile Gln Glu Arg Asp Glu Leu Ala Trp Lys
            100                 105                 110

Lys Leu Lys Leu Asp Gly Leu Asp Glu Asp Gly Glu Lys Glu Ala Arg
        115                 120                 125

Leu Ile Arg Asn Leu Asn Val Ile Leu Ala Lys Tyr Gly Leu Asp Gly
130                 135                 140

Lys Lys Asp Ala Arg Gln Val Thr Ser Asn Ser Leu Ser Gly Thr Gln
145                 150                 155                 160

Glu Asp Gly Leu Asp Asp Pro Arg Leu Glu Lys Leu Trp His Lys Ala
            165                 170                 175

Lys Thr Ser Gly Lys Phe Ser Gly Glu Glu Leu Asp Lys Leu Trp Arg
            180                 185                 190

Glu Phe Leu His His Lys Glu Lys Val His Glu Tyr Asn Val Leu Leu
        195                 200                 205

Glu Thr Leu Ser Arg Thr Glu Glu Ile His Glu Asn Val Ile Ser Pro
210                 215                 220

Ser Asp Leu Ser Asp Ile Lys Gly Ser Val Leu His Ser Arg His Thr
225                 230                 235                 240

Glu Leu Lys Glu Lys Leu Arg Ser Ile Asn Gln Gly Leu Asp Arg Leu
            245                 250                 255

Arg Arg Val Ser His Gln Gly Tyr Ser Thr Glu Ala Glu Phe Glu Glu
            260                 265                 270

Pro Arg Val Ile Asp Leu Trp Asp Leu Ala Gln Ser Ala Asn Leu Thr
        275                 280                 285

Asp Lys Glu Leu Glu Ala Phe Arg Glu Glu Leu Lys His Phe Glu Ala
290                 295                 300

Lys Ile Glu Lys His Asn His Tyr Gln Lys Gln Leu Glu Ile Ala His
305                 310                 315                 320

Glu Lys Leu Arg His Ala Glu Ser Val Gly Asp Gly Glu Arg Val Ser
            325                 330                 335

Arg Ser Arg Glu Lys His Ala Leu Leu Glu Gly Arg Thr Lys Glu Leu
            340                 345                 350

Gly Tyr Thr Val Lys Lys His Leu Gln Asp Leu Ser Gly Arg Ile Ser
        355                 360                 365

Arg Ala Arg His Asn Glu Leu Glu Arg Pro Val Pro Gly Ser Gly Ser
370                 375                 380

Ser Ala Tyr Tyr Asp Pro Asn Tyr Leu Thr Thr Val Glu Arg Pro Val
385                 390                 395                 400

Pro Gly Ser Asp Val Cys Glu Tyr Tyr Asp Pro Asp Tyr Leu Asn Thr
            405                 410                 415

Val Glu Arg Pro Val Pro Gly Ser Val Pro Val Ser Tyr Asp Ser
            420                 425                 430

Thr Tyr Leu Ser Thr
        435

<210> SEQ ID NO 135
<211> LENGTH: 465
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 135

```
Met Lys Arg Lys Ile Cys Lys Ala Leu Val Cys Ala Thr Leu Val Thr
1               5                   10                  15

Ser Leu Trp Ala Gly Val Ser Thr Lys Val Tyr Ala Trp Asp Gly Lys
            20                  25                  30

Ile Asp Gly Thr Gly Thr His Ala Met Ile Val Thr Gln Gly Val Ser
        35                  40                  45

Ile Leu Glu Asn Asp Met Ser Lys Asn Glu Pro Glu Ser Val Arg Lys
    50                  55                  60

Asn Leu Glu Ile Leu Lys Asp Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
    130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Val Gly Cys Lys Thr Asn Glu Asp Phe Tyr Ala Asp Ile Leu
        195                 200                 205

Lys Asn Lys Asp Phe Asn Ala Trp Ser Lys Glu Tyr Ala Arg Gly Phe
    210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Asn Asn Val Lys Glu Leu Val Ala
        275                 280                 285

Tyr Ile Ser Thr Ser Gly Glu Lys Asp Ala Gly Thr Asp Asp Tyr Met
    290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Ala Gly Ser Lys Asp Thr Tyr Thr
                325                 330                 335

Phe Lys Leu Lys Asp Glu Asn Leu Lys Ile Asp Ile Gln Asn Met
            340                 345                 350

Trp Ile Arg Lys Arg Lys Tyr Thr Ala Phe Pro Asp Ala Tyr Lys Pro
        355                 360                 365

Glu Asn Ile Lys Val Ile Ala Asn Gly Lys Val Val Asp Lys Asp
    370                 375                 380

Ile Asn Glu Trp Ile Ser Gly Asn Ser Thr Tyr Asn Ile Lys Ser Ser
385                 390                 395                 400
```

```
Gly Asp Leu Glu Arg Pro Val Pro Gly Ser Gly Ser Ser Ala Tyr Tyr
                405                 410                 415

Asp Pro Asn Tyr Leu Thr Thr Val Glu Arg Pro Val Pro Gly Ser Asp
            420                 425                 430

Val Cys Glu Tyr Tyr Asp Pro Asp Tyr Leu Asn Thr Val Glu Arg Pro
        435                 440                 445

Val Pro Gly Ser Val Pro Val Ser Tyr Asp Ser Thr Tyr Leu Ser
    450                 455                 460

Thr
465

<210> SEQ ID NO 136
<211> LENGTH: 347
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Asn Lys Val Lys Cys Tyr Val Leu Phe Thr Ala Leu Leu Ser Ser
1               5                   10                  15

Leu Cys Ala Tyr Gly Ala Ser Ser Tyr Ala His Gly Thr Pro Gln Asn
            20                  25                  30

Ile Thr Asp Leu Cys Ala Glu Ser His Asn Thr Gln Ile Tyr Thr Leu
        35                  40                  45

Asn Asp Lys Ile Phe Ser Tyr Thr Glu Ser Leu Ala Gly Lys Arg Glu
    50                  55                  60

Met Ala Ile Ile Thr Phe Lys Asn Gly Ala Ile Phe Gln Val Glu Val
65                  70                  75                  80

Pro Ser Ser Gln His Ile Asp Ser Gln Lys Lys Ala Ile Glu Arg Met
                85                  90                  95

Lys Asp Thr Leu Arg Ile Ala Tyr Leu Thr Glu Ala Lys Val Glu Lys
            100                 105                 110

Leu Cys Val Trp Asn Asn Lys Thr Pro His Ala Ile Ala Ala Ile Ser
        115                 120                 125

Met Ala Asn Gly Gly Ser Gly Val Pro Gly Ser Gly Gly Ser Gly Gln
    130                 135                 140

Ala Pro Leu Ser Leu Val Gln Pro Phe Arg Asp Ser Ala Ala Ala Asp
145                 150                 155                 160

Val Pro Gly Ser Gly Gly Ser Gly Tyr Ser Tyr Trp Asp Ser Thr Phe
                165                 170                 175

Leu Asp Thr Leu Ser Ala Ala Asp Val Pro Gly Ser Gly Gly Ser
            180                 185                 190

Gly Val Gly Ala Asp Val Gly Thr Leu Ser Ala Ala Phe Ser Ala Ala
        195                 200                 205

Ala Asp Val Pro Gly Ser Gly Gly Ser Gly Asp Val Gly Asp Leu Gly
    210                 215                 220

Arg Pro Val His Phe Ile Ser Ala Ala Ala Asp Val Pro Gly Ser Gly
225                 230                 235                 240

Gly Ser Gly Ala Pro Thr Ser Pro Val Thr His Gly Pro Gln Leu Ser
                245                 250                 255

Ala Ala Ala Asp Val Pro Gly Ser Gly Gly Ser Gly Ser Leu Thr Ser
            260                 265                 270

Pro Ile Thr Pro Arg Pro Glu Tyr Ser Ala Ala Ala Asp Val Pro Gly
```

```
            275                 280                 285
Ser Gly Gly Ser Gly Asp Phe Gly Asp His Asn Pro Pro Glu Gln Ser
    290                 295                 300

Ser Ser Ala Ala Ala Asp Val Pro Gly Ser Gly Ser Gly Asp Pro
305                 310                 315                 320

Thr Arg Phe His Ser Arg Pro Pro Ala Ile Ser Ala Ala Ala Asp Val
                325                 330                 335

Gln Leu Gln Val Glu His His His His His His
            340                 345
```

<210> SEQ ID NO 137
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Met Gly Ser Ser His His His His Ser Ser Gly Leu Val Pro
1               5                   10                  15

Arg Gly Ser His Met Leu Asp Met Ala Ser Ser Leu Arg Gln Ile Leu
                20                  25                  30

Asp Ser Gln Lys Met Glu Trp Arg Ser Asn Ala Gly Gly Ser Gly Arg
            35                  40                  45

Asp Asn Arg Val Ile Ser Arg Glu Lys Asn Gln Pro Lys Pro Ser Pro
    50                  55                  60

Lys Arg Glu Ser Gly Glu Glu Phe Arg Met Glu Lys Leu Asn Gln Leu
65                  70                  75                  80

Trp Glu Lys Ala Gln Arg Leu His Leu Pro Pro Val Arg Leu Ala Glu
                85                  90                  95

Leu His Ala Asp Leu Lys Ile Gln Glu Arg Asp Glu Leu Ala Trp Lys
            100                 105                 110

Lys Leu Lys Leu Asp Gly Leu Asp Glu Asp Gly Glu Lys Glu Ala Arg
        115                 120                 125

Leu Ile Arg Asn Leu Asn Val Ile Leu Ala Lys Tyr Gly Leu Asp Gly
    130                 135                 140

Lys Lys Asp Ala Arg Gln Val Thr Ser Asn Ser Leu Ser Gly Thr Gln
145                 150                 155                 160

Glu Asp Gly Leu Asp Asp Pro Arg Leu Glu Lys Leu Trp His Lys Ala
                165                 170                 175

Lys Thr Ser Gly Lys Phe Ser Gly Glu Leu Asp Lys Leu Trp Arg
            180                 185                 190

Glu Phe Leu His His Lys Glu Lys Val His Glu Tyr Asn Val Leu Leu
        195                 200                 205

Glu Thr Leu Ser Arg Thr Glu Glu Ile His Glu Asn Val Ile Ser Pro
    210                 215                 220

Ser Asp Leu Ser Asp Ile Lys Gly Ser Val Leu His Ser Arg His Thr
225                 230                 235                 240

Glu Leu Lys Glu Lys Leu Arg Ser Ile Asn Gln Gly Leu Asp Arg Leu
                245                 250                 255

Arg Arg Val Ser His Gln Gly Tyr Ser Thr Glu Ala Glu Phe Glu Glu
            260                 265                 270

Pro Arg Val Ile Asp Leu Trp Asp Leu Ala Gln Ser Ala Asn Leu Thr
        275                 280                 285
```

```
                    -continued

Asp Lys Glu Leu Glu Ala Phe Arg Glu Glu Leu Lys His Phe Glu Ala
    290             295                 300

Lys Ile Glu Lys His Asn His Tyr Gln Lys Gln Leu Glu Ile Ala His
305             310              315                     320

Glu Lys Leu Arg His Ala Glu Ser Val Gly Asp Gly Glu Arg Val Ser
                325                 330                 335

Arg Ser Arg Glu Lys His Ala Leu Leu Glu Gly Arg Thr Lys Glu Leu
                340             345                 350

Gly Tyr Thr Val Lys Lys His Leu Gln Asp Leu Ser Gly Arg Ile Ser
            355             360                 365

Arg Ala Arg His Asn Glu Leu Glu Arg Pro Val Pro Gly Ser Gly Gly
    370                 375             380

Ser Gly Gln Ala Pro Leu Ser Leu Val Gln Pro Phe Arg Asp Ser Ala
385             390                 395                 400

Ala Ala Asp Val Pro Gly Ser Gly Gly Ser Gly Tyr Ser Tyr Trp Asp
                405             410              415

Ser Thr Phe Leu Asp Thr Leu Ser Ala Ala Ala Asp Val Pro Gly Ser
            420             425                 430

Gly Gly Ser Gly Val Gly Ala Asp Val Gly Thr Leu Ser Ala Ala Phe
            435             440                 445

Ser Ala Ala Asp Val Pro Gly Ser Gly Gly Ser Gly Asp Val Gly
    450             455                 460

Asp Leu Gly Arg Pro Val His Phe Ile Ser Ala Ala Ala Asp Val Pro
465                 470              475                 480

Gly Ser Gly Gly Ser Gly Ala Pro Thr Ser Pro Val Thr His Gly Pro
                485                 490                 495

Gln Leu Ser Ala Ala Ala Asp Val Pro Gly Ser Gly Gly Ser Gly Ser
            500             505                 510

Leu Thr Ser Pro Ile Thr Pro Arg Pro Glu Tyr Ser Ala Ala Ala Asp
        515             520                 525

Val Pro Gly Ser Gly Gly Ser Gly Asp Phe Gly Asp His Asn Pro Pro
    530             535                 540

Glu Gln Ser Ser Ser Ala Ala Ala Asp Val Pro Gly Ser Gly Gly Ser
545             550                 555                 560

Gly Asp Pro Thr Arg Phe His Ser Arg Pro Pro Ala Ile Ser Ala Ala
                565             570              575

Ala Asp Val Gln Leu Asp
            580
```

The invention claimed is:

1. An antigenic composition comprising: a fusion protein comprising a carrier peptide and at least one epitope, wherein the carrier peptide is selected from the group consisting of Receptor Associated Protein (RAP) and *Clostridium perfringens* α-toxin, and wherein the epitope comprises a botulinum neurotoxin (BoNT) epitope or a mimetic BoNT epitope capable of eliciting an immune response in a human or animal subject.

2. The composition of claim 1, wherein the fusion protein specifically binds to an anti-BoNT antibody.

3. The composition of claim 1, wherein the BoNT epitope is selected from the group consisting of SEQ ID NOs: 19, 20, 22, 24, 25, 29, 30, 31, 102 and 118.

4. The composition of claim 1 further comprising: multiple BoNT epitopes and/or multiple mimetic BoNT epitopes.

5. The composition of claim 4, wherein the BoNT epitopes and/or mimetic BoNT epitopes are selected from the group consisting of SEQ ID NOs: 11-61 and 102-133.

6. A method for producing an antigenic composition comprising:
(a) expressing in a host cell a fusion protein comprising a carrier peptide and at least one epitope, wherein the carrier peptide is selected from the group consisting of Receptor Associated Protein (RAP) and *Clostridium perfringens* α-toxin; and
(b) isolating the fusion protein produced by the host, wherein the epitope comprises a botulinum neurotoxin (BoNT) epitope or a mimetic BoNT epitope capable of eliciting an immune response in a human or animal subject.

7. The method of claim 6, wherein the BoNT epitope is selected from the group consisting of SEQ ID NOs: 11-61 and 102-133.

8. The method of claim 6, wherein the fusion protein is expressed in the host cell from an expression vector.

9. The method of claim 8, wherein the expression vector is selected from the group consisting of a plasmid DNA, a viral vector, a bacterial vector, a mammalian vector, and a vector capable of integrating into the genome of the host cell.

10. The method of claim 6, wherein the fusion protein comprises a carrier peptide and multiple BoNT epitopes and/or multiple mimetic BoNT epitopes.

11. The method of claim 10, wherein the BoNT epitopes are selected from the group consisting of SEQ ID NOs: 11-61 and 102-133.

* * * * *